United States Patent
Armstrong

(10) Patent No.: US 7,996,079 B2
(45) Date of Patent: Aug. 9, 2011

(54) INPUT RESPONSE OVERRIDE FOR AN IMPLANTABLE MEDICAL DEVICE

(75) Inventor: Randolph K. Armstrong, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 973 days.

(21) Appl. No.: 11/338,548

(22) Filed: Jan. 24, 2006

(65) Prior Publication Data

US 2007/0173910 A1 Jul. 26, 2007

(51) Int. Cl.
*A61N 1/08* (2006.01)

(52) U.S. Cl. ............................. 607/2; 607/60
(58) Field of Classification Search .............. 607/2, 60
See application file for complete search history.

(56) References Cited

U.S. PATENT DOCUMENTS

| | | | |
|---|---|---|---|
| 3,760,812 A | 9/1973 | Timm et al. |
| 3,796,221 A | 3/1974 | Hagfors |
| 4,107,469 A | 8/1978 | Jenkins |
| 4,305,402 A | 12/1981 | Katims |
| 4,338,945 A | 7/1982 | Kosugi et al. |
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,541,432 A | 9/1985 | Molina-Negro et al. |
| 4,573,481 A | 3/1986 | Bullara |
| 4,577,316 A | 3/1986 | Schiff |
| 4,590,946 A | 5/1986 | Loeb |
| 4,592,339 A | 6/1986 | Kuzmak et al. |
| 4,606,349 A | 8/1986 | Livingston et al. |
| 4,608,985 A | 9/1986 | Crish et al. |
| 4,612,934 A | 9/1986 | Borkan |
| 4,625,308 A | 11/1986 | Kim et al. |
| 4,628,942 A | 12/1986 | Sweeney et al. |
| 4,649,936 A | 3/1987 | Ungar et al. |
| 4,702,254 A | 10/1987 | Zabara |
| 4,735,204 A * | 4/1988 | Sussman et al. ............. 607/60 |
| 4,793,353 A | 12/1988 | Borkan |
| 4,867,164 A | 9/1989 | Zabara |
| 4,920,979 A | 5/1990 | Bullara |
| 4,949,721 A | 8/1990 | Toriu et al. |
| 4,977,985 A | 12/1990 | Wells et al. |
| 5,025,807 A | 6/1991 | Zabara |
| 5,081,987 A | 1/1992 | Nigam |

(Continued)

FOREIGN PATENT DOCUMENTS

CA 2339971 6/2004

(Continued)

OTHER PUBLICATIONS

Lockard et al., "Feasibility And Safety Of Vagal Stimulation In Monkey Model;" Epilepsia, vol. 31 (Supp. 2) (1990), pp. S20-S26.

(Continued)

*Primary Examiner* — Michael Kahelin
(74) *Attorney, Agent, or Firm* — Williams, Morgan + Amerson, P.C.; Darrell N. Fuller; Jonathan D. Rowell

(57) ABSTRACT

A method and apparatus for providing an override of an operational mode of an implantable medical device. An override input to enter an override mode is received. A determination as to whether a magnetic input has been received is made. A predetermined response to the magnetic input is blocked in response to receiving the override input.

11 Claims, 12 Drawing Sheets

U.S. PATENT DOCUMENTS

| | | |
|---|---|---|
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,222,494 A | 6/1993 | Baker, Jr. |
| 5,231,988 A | 8/1993 | Wernicke et al. |
| 5,235,980 A | 8/1993 | Varrichio et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,330,507 A | 7/1994 | Schwartz |
| 5,330,515 A | 7/1994 | Rutecki et al. |
| 5,334,221 A | 8/1994 | Bardy |
| 5,354,320 A | 10/1994 | Schaldach et al. |
| 5,411,531 A | 5/1995 | Hill et al. |
| 5,411,540 A | 5/1995 | Edell et al. |
| 5,423,872 A | 6/1995 | Cigaina |
| 5,507,784 A | 4/1996 | Hill et al. |
| 5,522,862 A | 6/1996 | Testerman et al. |
| 5,522,865 A | 6/1996 | Schulman et al. |
| 5,540,730 A | 7/1996 | Terry, Jr. et al. |
| 5,540,734 A | 7/1996 | Zabara |
| 5,571,150 A | 11/1996 | Wernicke et al. |
| 5,601,617 A | 2/1997 | Loeb et al. |
| 5,611,350 A | 3/1997 | John |
| 5,645,570 A | 7/1997 | Corbucci |
| 5,651,378 A | 7/1997 | Matheny et al. |
| 5,658,318 A | 8/1997 | Stroetmann et al. |
| 5,690,681 A | 11/1997 | Geddes et al. |
| 5,690,688 A | 11/1997 | Noren et al. |
| 5,690,691 A | 11/1997 | Chen et al. |
| 5,700,282 A | 12/1997 | Zabara |
| 5,702,428 A | 12/1997 | Tippey et al. |
| 5,702,429 A | 12/1997 | King |
| 5,707,400 A | 1/1998 | Terry, Jr. et al. |
| 5,755,750 A | 5/1998 | Petruska et al. |
| 5,792,212 A | 8/1998 | Weijand |
| 5,800,474 A | 9/1998 | Benabid et al. |
| 5,814,092 A | 9/1998 | King |
| 5,836,994 A | 11/1998 | Bourgeois |
| 5,861,014 A | 1/1999 | Familoni |
| 5,913,882 A | 6/1999 | King |
| 5,916,239 A | 6/1999 | Geddes et al. |
| 5,928,272 A | 7/1999 | Adkins et al. |
| 5,941,906 A | 8/1999 | Barreras, Sr. et al. |
| 5,995,868 A | 11/1999 | Dorfmeister et al. |
| 6,002,966 A | 12/1999 | Loeb et al. |
| 6,016,449 A | 1/2000 | Fischell et al. |
| 6,041,258 A | 3/2000 | Cigaina et al. |
| 6,083,249 A | 7/2000 | Familoni |
| 6,101,412 A | 8/2000 | Duhaylongsod |
| 6,104,955 A | 8/2000 | Bourgeois |
| 6,104,956 A | 8/2000 | Naritoku et al. |
| 6,115,628 A | 9/2000 | Stadler et al. |
| 6,132,361 A | 10/2000 | Epstein et al. |
| 6,141,590 A | 10/2000 | Renirie et al. |
| 6,161,044 A | 12/2000 | Silverstone |
| 6,167,311 A | 12/2000 | Rezai |
| 6,175,764 B1 | 1/2001 | Loeb et al. |
| 6,188,926 B1 * | 2/2001 | Vock ................................. 607/9 |
| 6,188,929 B1 | 2/2001 | Giordano |
| 6,219,580 B1 | 4/2001 | Faltys et al. |
| 6,221,908 B1 | 4/2001 | Kilgard et al. |
| 6,238,423 B1 | 5/2001 | Bardy |
| 6,249,704 B1 | 6/2001 | Maltan et al. |
| 6,253,109 B1 | 6/2001 | Gielen |
| 6,266,564 B1 | 7/2001 | Hill et al. |
| 6,269,270 B1 | 7/2001 | Boveja |
| 6,295,472 B1 | 9/2001 | Rubinstein et al. |
| 6,304,775 B1 | 10/2001 | Iasemidis et al. |
| 6,308,102 B1 | 10/2001 | Sieracki et al. |
| 6,324,421 B1 | 11/2001 | Stadler et al. |
| 6,327,503 B1 | 12/2001 | Familoni |
| 6,339,725 B1 | 1/2002 | Naritoku et al. |
| 6,341,236 B1 | 1/2002 | Osorio et al. |
| 6,353,762 B1 | 3/2002 | Baudino et al. |
| 6,356,788 B2 | 3/2002 | Boveja |
| 6,358,203 B2 | 3/2002 | Bardy |
| 6,366,813 B1 | 4/2002 | DiLorenzo |
| 6,366,814 B1 | 4/2002 | Boveja et al. |
| 6,374,140 B1 | 4/2002 | Rise |
| 6,381,493 B1 | 4/2002 | Stadler et al. |
| 6,381,496 B1 | 4/2002 | Meadows et al. |
| 6,381,499 B1 | 4/2002 | Taylor et al. |
| 6,418,344 B1 | 7/2002 | Rezai et al. |
| 6,425,852 B1 | 7/2002 | Epstein et al. |
| 6,438,423 B1 | 8/2002 | Rezai et al. |
| 6,449,512 B1 | 9/2002 | Boveja |
| 6,453,199 B1 | 9/2002 | Kobozev |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,417 B1 | 11/2002 | Levine |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,487,446 B1 | 11/2002 | Hill et al. |
| 6,505,074 B2 | 1/2003 | Boveja et al. |
| 6,522,928 B2 | 2/2003 | Whitehurst et al. |
| 6,532,388 B1 | 3/2003 | Hill et al. |
| 6,549,804 B1 | 4/2003 | Osorio et al. |
| 6,556,868 B2 | 4/2003 | Naritoku et al. |
| 6,564,102 B1 | 5/2003 | Boveja |
| 6,565,503 B2 | 5/2003 | Leysieffer et al. |
| 6,579,280 B1 | 6/2003 | Kovach et al. |
| 6,587,719 B1 | 7/2003 | Barrett et al. |
| 6,587,724 B2 | 7/2003 | Mann |
| 6,587,726 B2 | 7/2003 | Lurie et al. |
| 6,587,727 B2 | 7/2003 | Osorio et al. |
| 6,591,138 B1 | 7/2003 | Fischell et al. |
| 6,594,524 B2 | 7/2003 | Esteller et al. |
| 6,600,953 B2 | 7/2003 | Flesler et al. |
| 6,609,025 B2 | 8/2003 | Barrett et al. |
| 6,609,030 B1 | 8/2003 | Rezai et al. |
| 6,609,031 B1 | 8/2003 | Law et al. |
| 6,610,713 B2 | 8/2003 | Tracey |
| 6,611,715 B1 | 8/2003 | Boveja |
| 6,612,983 B1 | 9/2003 | Marchal |
| 6,615,081 B1 | 9/2003 | Boveja |
| 6,615,084 B1 | 9/2003 | Cigaina |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,656,960 B2 | 12/2003 | Puskas |
| 6,662,053 B2 | 12/2003 | Borkan |
| 6,668,191 B1 | 12/2003 | Boveja |
| 6,671,547 B2 | 12/2003 | Lyster et al. |
| 6,671,555 B2 | 12/2003 | Gielen et al. |
| 6,671,556 B2 | 12/2003 | Osorio et al. |
| 6,684,104 B2 | 1/2004 | Gordon et al. |
| 6,684,105 B2 | 1/2004 | Cohen et al. |
| 6,690,973 B2 | 2/2004 | Hill et al. |
| 6,690,974 B2 | 2/2004 | Archer et al. |
| 6,708,064 B2 | 3/2004 | Rezai |
| 6,721,603 B2 | 4/2004 | Zabara et al. |
| 6,731,979 B2 | 5/2004 | MacDonald |
| 6,731,986 B2 | 5/2004 | Mann |
| 6,754,536 B2 | 6/2004 | Swoyer et al. |
| 6,760,626 B1 | 7/2004 | Boveja |
| 6,764,498 B2 | 7/2004 | Mische |
| 6,768,969 B1 | 7/2004 | Nikitin et al. |
| 6,775,573 B2 | 8/2004 | Schuler et al. |
| 6,793,670 B2 | 9/2004 | Osorio et al. |
| 6,819,956 B2 | 11/2004 | DiLorenzo |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,895,278 B1 | 5/2005 | Gordon |
| 6,904,390 B2 | 6/2005 | Nikitin et al. |
| 6,907,295 B2 | 6/2005 | Gross et al. |

| | | |
|---|---|---|
| 6,920,357 B2 | 7/2005 | Osorio et al. |
| 6,934,580 B1 | 8/2005 | Osorio et al. |
| 6,944,501 B1 | 9/2005 | Pless |
| 6,961,618 B2 | 11/2005 | Osorio et al. |
| 7,006,859 B1 | 2/2006 | Osorio et al. |
| 7,006,872 B2 | 2/2006 | Gielen et al. |
| 7,050,856 B2 | 5/2006 | Stypulkowski |
| 7,054,686 B2 | 5/2006 | MacDonald |
| 7,146,217 B2 | 12/2006 | Firlik et al. |
| 7,167,750 B2 | 1/2007 | Knudson et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,787 B2 | 4/2007 | DiLorenzo |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,340,302 B1 | 3/2008 | Falkenberg et al. |
| 2003/0144706 A1* | 7/2003 | Funke .......................... 607/30 |
| 2005/0010269 A1* | 1/2005 | Lebel et al. ..................... 607/60 |
| 2005/0154435 A1 | 7/2005 | Stern et al. |
| 2005/0159789 A1 | 7/2005 | Brockway et al. |
| 2005/0161052 A1 | 7/2005 | Rezai et al. |
| 2005/0165458 A1 | 7/2005 | Boveja et al. |
| 2005/0177192 A1 | 8/2005 | Rezai et al. |
| 2005/0177200 A1 | 8/2005 | George et al. |
| 2005/0177206 A1 | 8/2005 | North et al. |
| 2005/0182389 A1 | 8/2005 | LaPorte et al. |
| 2005/0187590 A1 | 8/2005 | Boveja et al. |
| 2005/0187593 A1 | 8/2005 | Housworth et al. |
| 2005/0187796 A1 | 8/2005 | Rosenfeld et al. |
| 2005/0192644 A1 | 9/2005 | Boveja et al. |
| 2005/0197590 A1 | 9/2005 | Osorio et al. |
| 2005/0222631 A1 | 10/2005 | Dalal et al. |
| 2005/0228693 A1 | 10/2005 | Webb et al. |
| 2005/0240246 A1 | 10/2005 | Lee et al. |
| 2005/0245944 A1 | 11/2005 | Rezai |
| 2005/0245971 A1 | 11/2005 | Brockway et al. |
| 2005/0245990 A1 | 11/2005 | Roberson |
| 2005/0261542 A1 | 11/2005 | Riehl |
| 2005/0267550 A1 | 12/2005 | Hess et al. |
| 2005/0272280 A1 | 12/2005 | Osypka |
| 2005/0277872 A1 | 12/2005 | Colby, Jr. et al. |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0283208 A1 | 12/2005 | Von Arx et al. |
| 2005/0288600 A1 | 12/2005 | Zhang et al. |
| 2005/0288736 A1 | 12/2005 | Persen et al. |
| 2005/0288760 A1 | 12/2005 | Machado et al. |
| 2006/0009815 A1 | 1/2006 | Boveja et al. |
| 2006/0020292 A1 | 1/2006 | Goetz et al. |
| 2006/0020491 A1 | 1/2006 | Mongeon et al. |
| 2006/0041222 A1 | 2/2006 | Dewing et al. |
| 2006/0041223 A1 | 2/2006 | Dewing et al. |
| 2006/0041287 A1 | 2/2006 | Dewing et al. |
| 2006/0047205 A1 | 3/2006 | Ludomirsky et al. |
| 2006/0052843 A1 | 3/2006 | Elsner et al. |
| 2006/0058597 A1 | 3/2006 | Machado et al. |
| 2006/0064133 A1 | 3/2006 | Von Arx et al. |
| 2006/0064134 A1 | 3/2006 | Mazar et al. |
| 2006/0064143 A1 | 3/2006 | Von Arx et al. |
| 2006/0069322 A1 | 3/2006 | Zhang et al. |
| 2006/0074450 A1 | 4/2006 | Boveja et al. |
| 2006/0079936 A1 | 4/2006 | Boveja et al. |
| 2006/0079942 A1 | 4/2006 | Deno et al. |
| 2006/0079945 A1 | 4/2006 | Libbus |
| 2006/0085046 A1 | 4/2006 | Rezai et al. |
| 2006/0094971 A1 | 5/2006 | Drew |
| 2006/0095081 A1 | 5/2006 | Zhou et al. |
| 2006/0100667 A1 | 5/2006 | Machado et al. |
| 2006/0106430 A1 | 5/2006 | Fowler et al. |
| 2006/0106431 A1 | 5/2006 | Wyler et al. |
| 2006/0111644 A1 | 5/2006 | Guttag et al. |
| 2006/0122525 A1 | 6/2006 | Shusterman |
| 2006/0122667 A1 | 6/2006 | Chavan et al. |
| 2006/0122864 A1 | 6/2006 | Gottesman et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0161459 A9 | 7/2006 | Rosenfeld et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195155 A1 | 8/2006 | Firlik et al. |
| 2006/0195163 A1 | 8/2006 | KenKnight et al. |
| 2006/0200206 A1 | 9/2006 | Firlik et al. |
| 2006/0212091 A1 | 9/2006 | Lozano et al. |
| 2006/0217780 A1 | 9/2006 | Gliner et al. |
| 2006/0220839 A1 | 10/2006 | Fifolt et al. |
| 2006/0224067 A1 | 10/2006 | Giftakis et al. |
| 2006/0224191 A1 | 10/2006 | Dilorenzo |
| 2006/0241697 A1 | 10/2006 | Libbus et al. |
| 2006/0241725 A1 | 10/2006 | Libbus et al. |
| 2006/0253164 A1 | 11/2006 | Zhang et al. |
| 2006/0253168 A1 | 11/2006 | Wyler et al. |
| 2006/0253169 A1 | 11/2006 | Wyler et al. |
| 2006/0253170 A1 | 11/2006 | Wyler et al. |
| 2006/0253171 A1 | 11/2006 | Wyler et al. |
| 2006/0259095 A1 | 11/2006 | Wyler et al. |
| 2006/0264730 A1 | 11/2006 | Stivoric et al. |
| 2006/0265018 A1 | 11/2006 | Smith et al. |
| 2006/0271409 A1 | 11/2006 | Rosenfeld et al. |
| 2006/0293720 A1 | 12/2006 | DiLorenzo |
| 2007/0027486 A1 | 2/2007 | Armstrong |
| 2007/0032734 A1 | 2/2007 | Najafi et al. |
| 2007/0032834 A1 | 2/2007 | Gliner et al. |
| 2007/0038262 A1 | 2/2007 | Kieval et al. |
| 2007/0043392 A1 | 2/2007 | Gliner et al. |
| 2007/0055320 A1 | 3/2007 | Weinand |
| 2007/0073150 A1 | 3/2007 | Gopalsami et al. |
| 2007/0073346 A1 | 3/2007 | Corbucci |
| 2007/0073355 A1 | 3/2007 | Dilorenzo |
| 2007/0078491 A1 | 4/2007 | Siejko et al. |
| 2007/0088403 A1 | 4/2007 | Wyler et al. |
| 2007/0088404 A1 | 4/2007 | Wyler et al. |
| 2007/0088405 A1 | 4/2007 | Jacobson |
| 2007/0100278 A1 | 5/2007 | Frei et al. |
| 2007/0100397 A1 | 5/2007 | Seeberger et al. |
| 2007/0100398 A1 | 5/2007 | Sloan |
| 2007/0112393 A1 | 5/2007 | Gliner |
| 2007/0123946 A1 | 5/2007 | Masoud |
| 2007/0135855 A1 | 6/2007 | Foshee et al. |
| 2007/0142862 A1 | 6/2007 | Dilorenzo |
| 2007/0142873 A1 | 6/2007 | Esteller et al. |
| 2007/0149952 A1 | 6/2007 | Bland et al. |
| 2007/0150011 A1 | 6/2007 | Meyer et al. |
| 2007/0150014 A1 | 6/2007 | Kramer et al. |
| 2007/0150024 A1 | 6/2007 | Leyde et al. |
| 2007/0150025 A1 | 6/2007 | Dilorenzo et al. |
| 2007/0156179 A1 | 7/2007 | S.E. |
| 2007/0156450 A1 | 7/2007 | Roehm et al. |
| 2007/0156626 A1 | 7/2007 | Roehm et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0179534 A1 | 8/2007 | Firlik et al. |
| 2007/0179584 A1 | 8/2007 | Gliner |
| 2007/0203548 A1 | 8/2007 | Pawelzik et al. |
| 2007/0208212 A1 | 9/2007 | DiLorenzo |
| 2007/0208390 A1 | 9/2007 | Von Arx et al. |
| 2007/0213785 A1 | 9/2007 | Osorio et al. |
| 2007/0233192 A1 | 10/2007 | Craig |
| 2007/0238939 A1 | 10/2007 | Giftakis et al. |
| 2007/0239210 A1 | 10/2007 | Libbus et al. |
| 2007/0239211 A1 | 10/2007 | Lorincz et al. |
| 2007/0239220 A1 | 10/2007 | Greenhut et al. |
| 2007/0244407 A1 | 10/2007 | Osorio |
| 2007/0249953 A1 | 10/2007 | Frei et al. |
| 2007/0249954 A1 | 10/2007 | Virag et al. |
| 2007/0250130 A1 | 10/2007 | Ball et al. |
| 2007/0250145 A1 | 10/2007 | Kraus et al. |
| 2007/0255147 A1 | 11/2007 | Drew et al. |
| 2007/0255155 A1 | 11/2007 | Drew et al. |

| Pub. No. | Date | Inventor |
|---|---|---|
| 2007/0255330 A1 | 11/2007 | Lee et al. |
| 2007/0255337 A1 | 11/2007 | Lu |
| 2007/0260147 A1 | 11/2007 | Giftakis et al. |
| 2007/0260289 A1 | 11/2007 | Giftakis et al. |
| 2007/0265489 A1 | 11/2007 | Fowler et al. |
| 2007/0265508 A1 | 11/2007 | Sheikhzadeh-Nadjar et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2007/0287931 A1 | 12/2007 | Dilorenzo |
| 2007/0288072 A1 | 12/2007 | Pascual-Leone et al. |
| 2007/0299349 A1 | 12/2007 | Alt et al. |
| 2007/0299473 A1 | 12/2007 | Matos |
| 2007/0299480 A1 | 12/2007 | Hill |
| 2008/0015651 A1 | 1/2008 | Ettori et al. |
| 2008/0015652 A1 | 1/2008 | Maile et al. |
| 2008/0021332 A1 | 1/2008 | Brainard, III |
| 2008/0021341 A1 | 1/2008 | Harris et al. |
| 2008/0021517 A1 | 1/2008 | Dietrich |
| 2008/0021520 A1 | 1/2008 | Dietrich |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0033503 A1 | 2/2008 | Fowler et al. |
| 2008/0033508 A1 | 2/2008 | Frei et al. |
| 2008/0039895 A1 | 2/2008 | Fowler et al. |
| 2008/0046035 A1 | 2/2008 | Fowler et al. |
| 2008/0046037 A1 | 2/2008 | Haubrich et al. |
| 2008/0046038 A1 | 2/2008 | Hill et al. |
| 2008/0051852 A1 | 2/2008 | Dietrich et al. |
| 2008/0058884 A1 | 3/2008 | Matos |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0081962 A1 | 4/2008 | Miller et al. |
| 2008/0082132 A1 | 4/2008 | Annest et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | LeBoeuf et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0183245 A1 | 7/2008 | Van Oort et al. |
| 2008/0195175 A1 | 8/2008 | Balzer et al. |
| 2008/0200925 A1 | 8/2008 | Johnson et al. |
| 2008/0208013 A1 | 8/2008 | Zhang et al. |
| 2008/0208074 A1 | 8/2008 | Snyder et al. |
| 2008/0208285 A1 | 8/2008 | Fowler et al. |
| 2008/0208291 A1 | 8/2008 | Leyde et al. |
| 2008/0208781 A1 | 8/2008 | Snyder |
| 2008/0215112 A1 | 9/2008 | Firlik et al. |
| 2008/0215114 A1 | 9/2008 | Stuerzinger et al. |
| 2008/0221644 A1 | 9/2008 | Vallapureddy et al. |
| 2008/0234598 A1 | 9/2008 | Snyder et al. |
| 2008/0249591 A1 | 10/2008 | Gaw et al. |
| 2008/0255582 A1 | 10/2008 | Harris |
| 2009/0054795 A1 | 2/2009 | Misczynski et al. |
| 2009/0076567 A1 | 3/2009 | Fowler et al. |

FOREIGN PATENT DOCUMENTS

| | | |
|---|---|---|
| EP | 0402683 A2 | 12/1990 |
| EP | 0713714 A2 | 5/1996 |
| EP | 1647300 A2 | 2/1998 |
| EP | 1070518 A2 | 1/2001 |
| EP | 1120130 A2 | 1/2001 |
| EP | 1145736 A2 | 10/2001 |
| EP | 1595497 A1 | 5/2004 |
| EP | 1486232 A2 | 12/2004 |
| GB | 2026870 A | 2/1980 |
| GB | 2079610 A | 1/1982 |
| WO | 9302744 A1 | 2/1993 |
| WO | 9417771 A2 | 8/1994 |
| WO | 9825688 A1 | 6/1998 |
| WO | 0040143 A1 | 7/2000 |
| WO | 0064336 A1 | 11/2000 |
| WO | 0105467 A1 | 1/2001 |
| WO | 0108749 A1 | 2/2001 |
| WO | 0064336 A9 | 6/2002 |
| WO | 03076010 A1 | 9/2003 |
| WO | 03085546 A1 | 10/2003 |
| WO | 2004036377 A2 | 4/2004 |
| WO | 2004064918 A1 | 8/2004 |
| WO | 2004069330 A1 | 8/2004 |
| WO | 2004071575 A1 | 8/2004 |
| WO | 2004075982 A1 | 9/2004 |
| WO | 2004112894 A1 | 12/2004 |
| WO | 2005007120 A2 | 1/2005 |
| WO | 2005007232 A2 | 1/2005 |
| WO | 2005028026 A1 | 3/2005 |
| WO | 2005053788 A1 | 6/2005 |
| WO | 2005067599 A2 | 7/2005 |
| WO | 2005101282 A2 | 10/2005 |
| WO | 2006014760 A1 | 2/2006 |
| WO | 2006019822 A2 | 2/2006 |
| WO | 2006050144 A1 | 5/2006 |
| WO | 2006122148 A2 | 11/2006 |
| WO | 2007066343 A2 | 6/2007 |
| WO | 2007072425 A2 | 6/2007 |
| WO | 2007124126 A2 | 11/2007 |
| WO | 2007124190 A2 | 11/2007 |
| WO | 2007124192 A1 | 11/2007 |
| WO | 2007142523 A1 | 12/2007 |

OTHER PUBLICATIONS

Bachman, D.,S. et al.; "Effects Of Vagal Volleys And Serotonin On Units Of Cingulate Cortex in Monkeys;" Brain Research , vol. 130 (1977). pp. 253-269.

Terry et al.; "The Implantable Neurocybernetic Prosthesis System", Pacing and Clinical Electrophysiology, vol. 14, No. 1 (Jan. 1991), pp. 86-93.

Bohning, D.E., et al.; "Feasibility of Vagus Nerve Stimulation—Synchronized Blood Oxygenation Level-Dependent Functional MRI;" A Journal of Clinical and Laboratory Research: Investigative Radiology; vol. 36, No. 8 (Aug. 2001); pp. 470-479.

Boon, Paul, et al.; "Programmed and Magnet-Induced Vagus Nerve Stimulation for Refractory Epilepsy;" Journal of Clinical Neurophysiology vol. 18 No. 5; (2001); pp. 402-407.

Clark, K.B., et al.; "Posttraining Electrical Stimulation of Vagal Afferents with Concomitant Vagal Efferent Inactivation Enhances Memory Storage Processes in the Rat;" Neurobiology of Learning and Memory, vol. 70, 364-373 (1998) Art. No. NL983863.

Clark, K.B., et al.; "Enhanced Recognition Memory Following Vagus Nerve Stimulation in Human Subjects;" Nature Neuroscience, vol. 2, No. 1, (Jan. 1999) pp. 93-98.

DeGiorgo, Christopher M., et al.; "Vagus Nerve Stimulation: Analysis of Device Parameters in 154 Patients During the Long-Term XE5 Study;" Epilepsia, vol. 42, No. 8; pp. 1017-1020 (2001).

Devous, Michael D., et al.; "Effects of Vagus Nerve Stimulation on Regional Cerebral Blood Flow in Treatment-Resistant Depression;" National Institute of Mental Health—42nd Annual NCDEU Meeting: Poster Session II; Poster Abstracts, Jun. 10-13, 2002, 1 page; http://www.nimh.nih.gov/ncdeu/abstracts2002/ncdeu2019.cfm.

Dodrill, Ph.D., et al.; "Effects of Vagal Nerve Stimulation on Cognition and Quality of Life in Epilepsy;" Epilepsy and Behavior, vol. 2 (2001); pp. 46-53.

Fanselow, E. E., et al.; "Reduction of Pentylenetetrazole-Induced Seizure Activity in Awake Rats by Seizure-Triggered Trigeminal Nerve Stimulation;" The Journal of Neuroscience, vol. 20, No. 21; (Nov. 2000); pp. 8160-8168.

George, M.S., et al.; "Open Trial of VNS Therapy in Severe Anxiety Disorders;" 156th American Psychiatric Association Annual Meeting; May 17-22, 2003.

George, M.S., et al.; "Vagus Nerve Stimulation: A New Tool for Brain Research and Therapy;" Society of Biological Psychiatry vol. 47 (2000) pp. 287-295.

Hallowitz, R.A., et al.; "Effects Of Vagal Volleys On Units Of Intralaminar and Juxtalaminar Thalamic Nuclei in Monkeys;" Brain Research, vol. 130 (1977), pp. 271-286.

Henry, MD, T.R.; "Therapeutic Mechanisms of Vagus Nerve Stimulation" Neurology, vol. 59 Suppl. 4 (Sep. 2002); pp. S3-S14.

King, M.D., "Effects of Short-Term Vagus Nerve Stimulation (VNS) on FOS Expression in Rat Brain Nuclei" 58th Annual Scientific Convention of the Society of Biological Psychiatry, (May 2003).

Klapper, M.D., et al., "VNS Therapy Shows Potential Benefit in Patients with Migraine and Chronic Daily Headache After 3 to 6 Months of Treatment (Preliminary Results)" 45th Annual Scientific Meeting of the American Headache Society (Jun. 2003).

Koo, B., "EEG Changes With Vagus Nerve Stimulation" Journal of Clinical Neurophysiology, vol. 18 No. 5 (Sep. 2001); pp. 434-441.

Labar, D., "Vagus Nerve Stimulation for 1 Year in 269 patients on Unchanged Antiepilectic Drugs" Seizure vol. 13, (2004) pp. 392-398.

Liebman, K.M. et al.; "Improvement in Cognitive Function After Vagal Nerve Stimulator Implantation;" Epilepsia, vol. 39, Suppl. 6 (1998) 1 page.

Malow, B.A., et al.; "Vagus Nerve Stimulation Reduces Daytime Sleepiness in Epilepsy Patients" Neurology 57 (2001) pp. 879-884.

McClintock, P., "Can Noise Actually Boost Brain Power" Physics World Jul. 2002; pp. 20-21.

Mori, T., et al.; "Noise-Induced Entrainment and Stochastic Resonance in Human Brain Waves" Physical Review Letters vol. 88, No. 21 (May 2002); pp. 218101-1-218101-4.

Rugg-Gunn, F.J., et al.; "Cardiac Arrhythmias in Focal Epilepsy: a Prospective Long-Term Study" www.thelancet.com vol. 364 (2004) pp. 2212-2219.

Rutecki, P.; "Anatomical, Physiological, and Theoretical Basis for the Antiepileptic Effect of Vagus Nerve Stimulation" Epilepsia, vol. 31 Suppl. 2; S1-S6 (1990).

Sahin, M.; et al.; "Improved Nerve Cuff Electrode Recordings with Subthreshold Anodic Currents;" IEEE Transactions on Biomedical Engineering, vol. 45, No. 8 (Aug. 1998) pp. 1044-1050.

Schachter, S.C., et al.; "Progress in Epilepsy Research: Vagus Nerve Stimulation;" Epilepsia, vol. 39, No. 7 (1998) pp. 677-686.

Tatum, W.O., et al.; "Ventricular Asystole During Vagus Nerve Stimulation for Epilepsy in Humans" American Academy of Neurologgy (1999) p. 1267 (See also pp. 1117, 1166, and 1265).

Tatum, W.O., et al.; "Vagus Nerve Stimulation and Drug Reduction" Neurology, vol. 56, No. 4 (Feb. 2001) pp. 561-563.

Tubbs, R.S., et al.; "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag 2004.

Valdes-Cruz, A., et al.; "Chronic Stimulation of the Cat Vagus Nerve Effect on Sleep and Behavior" Progress in Neuro-Psychopharmacology & Biological Psychiatry, vol. 26 (2002) pp. 113-118.

Vonck et al. "The Mechanism of Action Of Vagus Nerve Stimulation For Refractory Epilepsy", Journal of Clinical Neurophysiology, vol. 18(5) (2001), pp. 394-401.

Ward, H., M.D., et al.; "Treatment-Refractory Obsessive-Compulsive Disorder: Potential Benefit of VNS Therapy" 23rd Annual Conference of the Anxiety Disorders Association of America (2007).

Zabara, J. "Inhibition of Experimental Seizures in Canines by Repetivie Vagal Stimulation" Epilepsia vol. 33, No. 6 (1992); pp. 1005-1012.

Craig, A.D. (BUD); "Distribution of Trigeminothalamic and Spinothalamic Lamina I Terminations in the Macaque Monkey;" The Journal of Comparative Neurology, vol. 477, pp. 119-148 (2004).

Harry, J.D., et al.; "Balancing Act: Noise is the Key to Restoring the Body's Sense of Equilibrium;" IEEE Spectrum (Apr. 2005) pp. 37-41.

Henry, T.R., et al.; "Brain Blood-Flow Alterations Induced by Therapeutic Vagus Nerve Stimulation in Partial Epilepsy: I. Acute Effects at High and Low Levels of Stimulation;" Epilepsia vol. 39, No. 9; pp. 984-990 (1998).

Woodbury, et al., "Vagal Stimulation Reduces the Severity Of Maximal Electroshock Seizures in Intact Rats. Use of a Cuff Electrode for Stimulating And Recording"; Pacing and Clinical Electrophysiology, vol. 14 (Jan. 1991), pp. 94-107.

Fromes, G., et al.; "Clinical Utility of On-Demand Magnet Use with Vagus Nerve Stimulation;" AES Proceedings 2.109; Epilepsia 41S7, p. 117 (2000).

\* cited by examiner

INPUT RESPONSE OVERRIDE FOR AN IMPLANTABLE MEDICAL DEVICE

CROSS-REFERENCE TO RELATED APPLICATION

This application is a related application to U.S. patent application Ser. No. 11/338,374, entitled "Stimulation Mode Adjustment For An Implantable Medical Device," which is filed on the same date as the present application and in the name of the same inventor.

BACKGROUND OF THE INVENTION

1. Field of the Invention

This invention relates generally to implantable medical devices, and, more particularly, to methods, apparatus, and systems for performing an override of a normal operation of an implantable medical device.

2. Description of the Related Art

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied at strategic locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. Nos. 4,702,254, 4,867,164, and 5,025,807 to Dr. Jacob Zabara, which are hereby incorporated in their entirety herein by reference in this specification.

More generally, the endogenous electrical activity (i.e., activity attributable to the natural functioning of the patient's own body) of a neural structure of a patient may be modulated in a variety of ways. In particular, the electrical activity may be modulated by exogenously applied (i.e., from a source other than the patient's own body) electrical, chemical, or mechanical signals applied to the neural structure. The modulation (hereinafter referred to generally as "neurostimulation" or "neuromodulation") may involve the induction by the generation of afferent action potentials, efferent action potentials, or both, in the neural structure, and may also involve blocking or interrupting the transmission of endogenous electrical activity traveling along the nerve. Electrical neurostimulation or modulation of a neural structure refers to the application of an exogenous electrical signal (as opposed to a chemical or mechanical signal), to the neural structure. Electrical neurostimulation may be provided by implanting an electrical device underneath the skin of a patient and delivering an electrical signal to a nerve such as a cranial nerve. The electrical neurostimulation may involve performing a detection, with the electrical signal being delivered in response to a detected body parameter. This type of stimulation is generally referred to as "active," "feedback," or "triggered" stimulation. Alternatively, the system may operate without a detection system once the patient has been diagnosed with epilepsy (or another medical condition), and may periodically apply a series of electrical pulses to the nerve (e.g., a cranial nerve such as a vagus nerve) intermittently throughout the day, or over another predetermined time interval. This type of stimulation is generally referred to as "passive," "non-feedback," or "prophylactic," stimulation. The stimulation may be applied by an implantable medical device that is implanted within the patient's body, or by a device that is external to the patient's body, with a radio frequency (RF) coupling to an implanted electrode.

Generally, implantable medical devices (IMD) are capable of receiving a signal that may affect the operation of the IMD, from sources external to the IMD, such as a patient-initiated signal or a signal in the patient's environment. For example, a magnetic sensor may be provided in the IMD to detect a significant magnetic field, and in response, activate a predetermined function. A magnetic signal input from a patient may include an inhibitory input or an excitatory input. The inhibitory input may relate to inhibiting a function normally performed by the IMD. For example, application of a particular magnetic field to the IMD may cause delivery of the electrical signal from the IMD to the nerve to be inhibited for a certain time period. Application of a different magnetic field signal to the IMD may prompt the IMD to perform additional functions. For example, additional stimulation therapy delivery may be performed by the IMD based upon a particular magnetic signal input. The magnetic signal input may be generated by a patient by placing a magnet proximate the skin area under which the implantable medical device resides in the human body. Both types of magnetic field signals are typically referred to as "magnet modes" or as "magnet mode" operation.

One problem associated with current magnet mode approaches results from external magnetic fields that are not intended by the patient to function as a magnetic signal input to the IMD. Thus, if a patient encounters an external magnetic field, such as a magnetic resonance imaging (MRI) signal, or other strong magnetic or electromagnetic fields, normal operations performed by the stimulation by the IMD may be affected. This could cause inadvertent inhibition of the delivery by the IMD of the electrical signal to the nerve, or inadvertent alteration of the neurostimulation therapy. A person entering an area of magnetic activity or fluctuations may cause an IMD to experience false inputs. Current IMD configurations generally lack an effective method of overriding such false inputs.

The present invention is directed to overcoming, or at least reducing, the effects of one or more of the problems set forth above.

SUMMARY OF THE INVENTION

In one aspect, the present invention comprises a method for providing an override of an operational mode of an implantable medical device. An override input to enter an override mode is received. A determination as to whether a magnetic input has been received is made. A predetermined response to the magnetic input is blocked in response to receiving the override input.

In another aspect, the present invention comprises a method for providing an override of a response function to a magnetic input in an implantable medical device (IMD) for delivering a neurostimulation therapy, is provided. The presence of a magnetic field is detected. A determination is made as to whether said IMD is in an override mode. The neurostimulation therapy is continued if said IMD is in an override mode.

In yet another aspect, the present invention comprises an implantable medical device (IMD) for providing an electrical neurostimulation therapy to a neural structure of a patient's body. The IMD includes a sensor to detect the presence of a magnetic field and an interface to receive an override signal for placing said IMD into an override mode. The IMD also includes a controller operatively coupled to said sensor and said interface, to determine whether a magnetic input has been received and to block a predetermined response to said magnetic input in response to receiving said override signal.

In yet another aspect, the present invention comprises an implantable medical device (IMD) for providing an operational override. The IMD includes means for receiving an override input to enter an override mode; means for determining whether a magnetic input has been received; and means for blocking a predetermined response to said magnetic input in response to receiving said override input.

BRIEF DESCRIPTION OF THE DRAWINGS

The invention may be understood by reference to the following description taken in conjunction with the accompanying drawings, in which like reference numerals identify like elements, and in which.

Figure 1A:
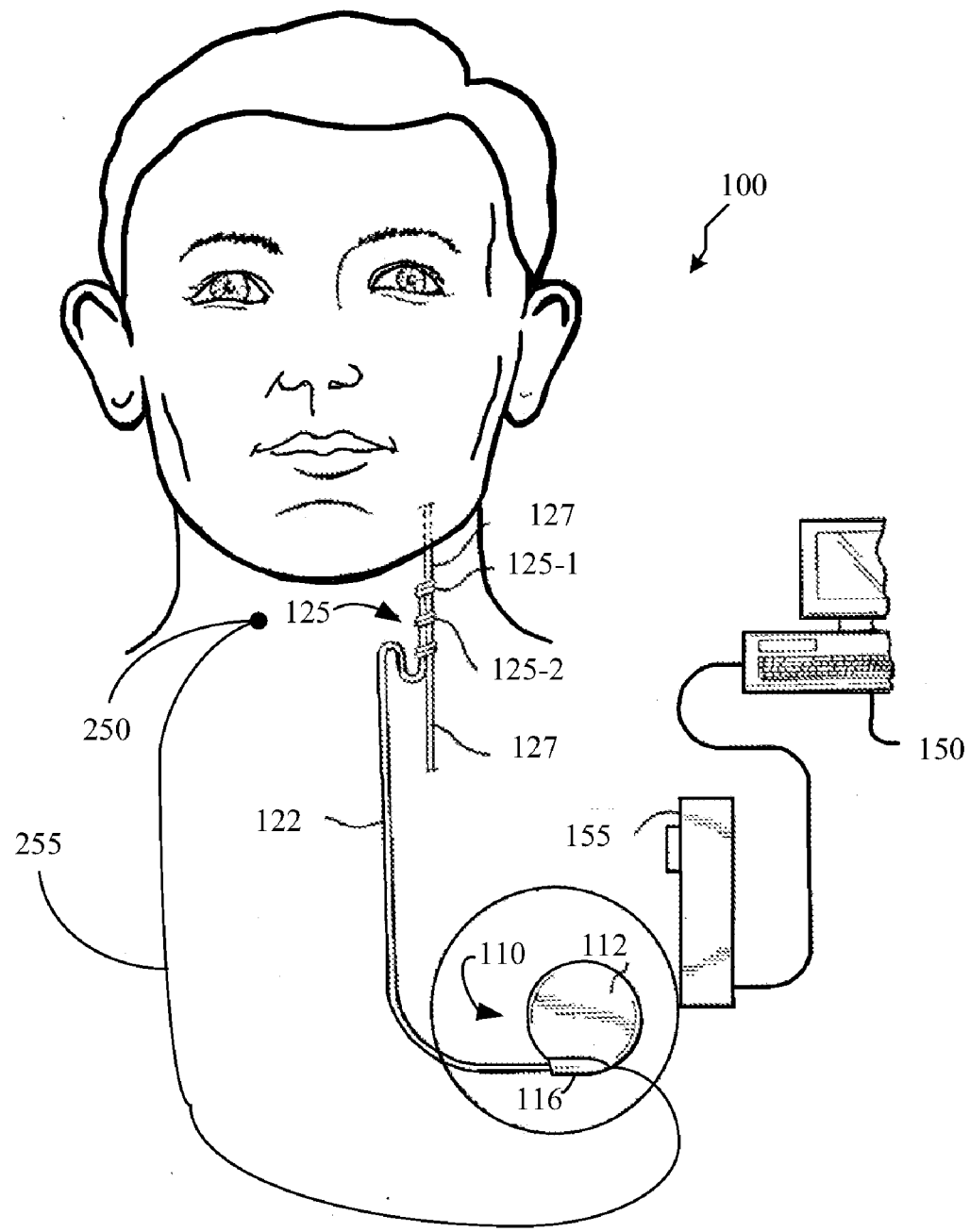
FIGS. 1A-1D provide stylized diagrams of an implantable medical device implanted into a patient's body for providing an electrical signal to a portion of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Embodiments of the present invention provide for performing an override of a normal operation of an implantable medical device (IMD). The normal operation mode or "normal operational mode" may be simply referred to as "operational mode" of the IMD. An input from an external source (e.g., a patient) may temporarily cause the IMD to exit the operational mode and enter into an alternative mode of operation (i.e., an override mode). This alternative mode of operation or the override mode may include temporarily disabling any stimulation. Alternatively, the alternative mode of operation or the override mode may include overriding a magnetic input that would have temporarily seized stimulation activities. This way, if the patient enters an area of significant magnetic activity, the IMD continues to perform normally. In an alternative embodiment of the present invention, the alternative mode of operation may include a reduced stimulation mode, such as a background stimulation process or other modification of a characteristic of the stimulation signal. Another embodiment of the present invention provides for an input to the IMD that would prompt the IMD to operate in an alternative/override mode for a predetermined period of time, or until another triggering input is received. Embodiments of the present invention provides for flexibility in controlling the operation of the IMD.

Although not so limited, a system capable of implementing embodiments of the present invention is described below. FIGS. 1A-1D depict a stylized implantable medical system 100 for implementing one or more embodiments of the present invention. FIGS. 1A-1D illustrate an electrical signal generator 110 having main body 112 comprising a case or shell 121 (FIG. 1C) with a header 116 (FIG. 1C) for connecting to leads 122. The generator 110 is implanted in the patient's chest in a pocket or cavity formed by the implanting surgeon just below the skin (indicated by a dotted line 145, FIG. 1B), similar to the implantation procedure for a pacemaker pulse generator.

Figure 1B:
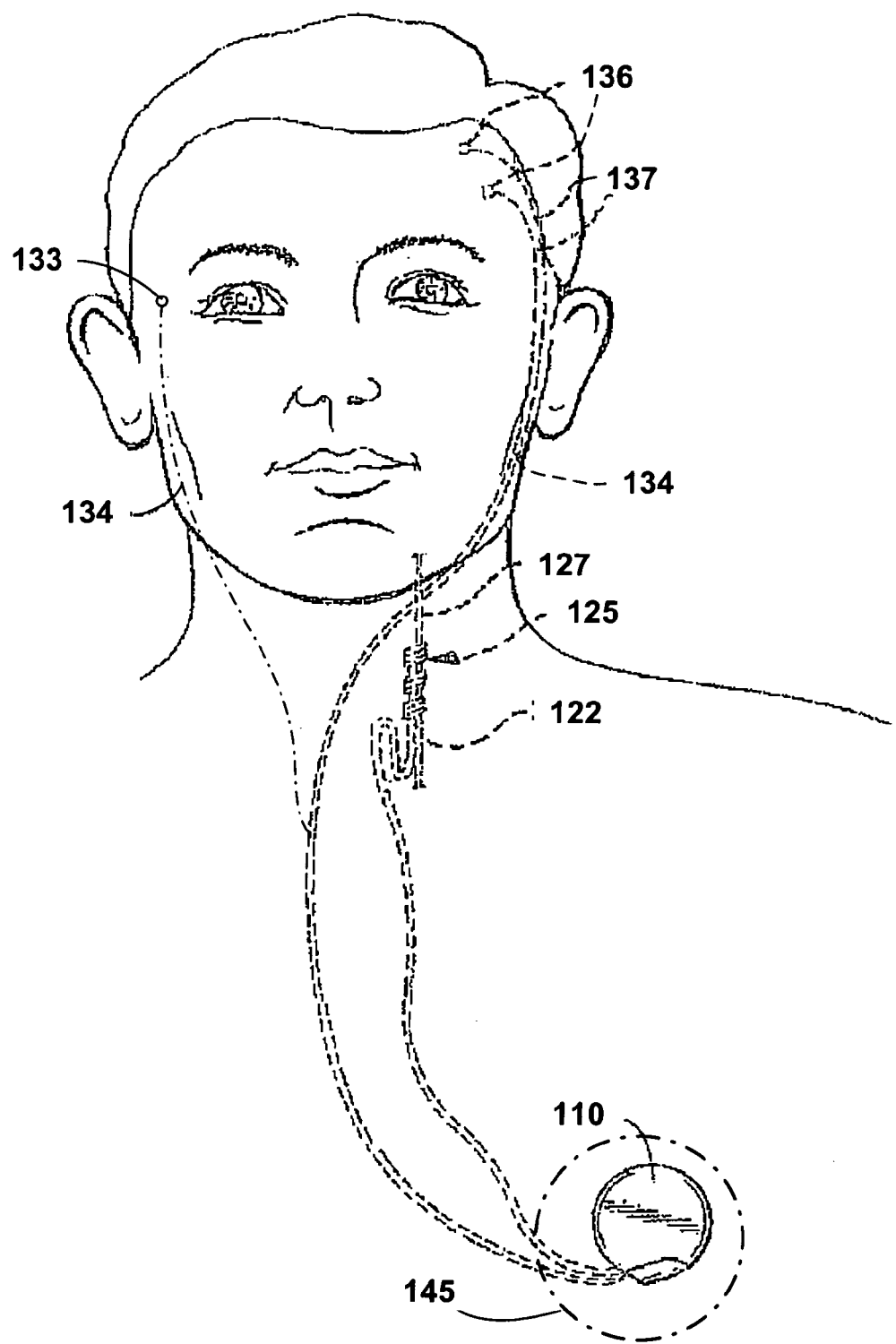
Figure 1C:
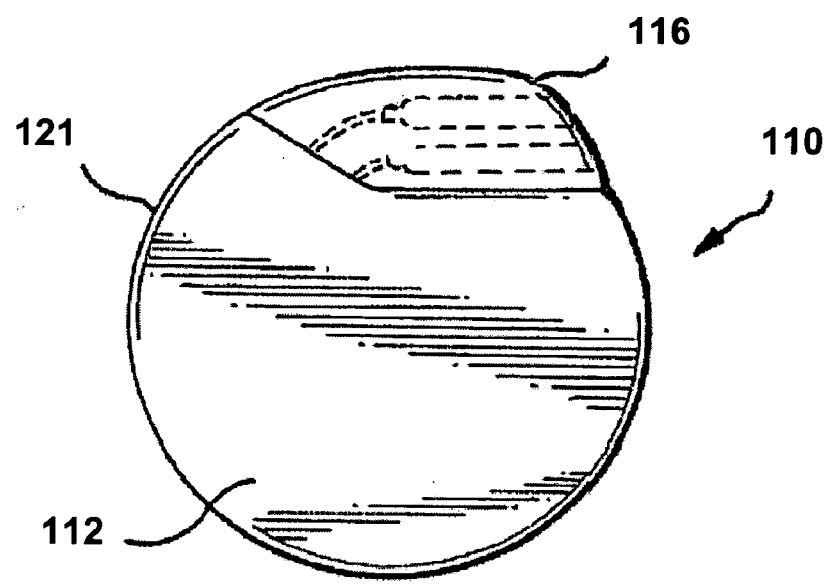
Figure 1D:
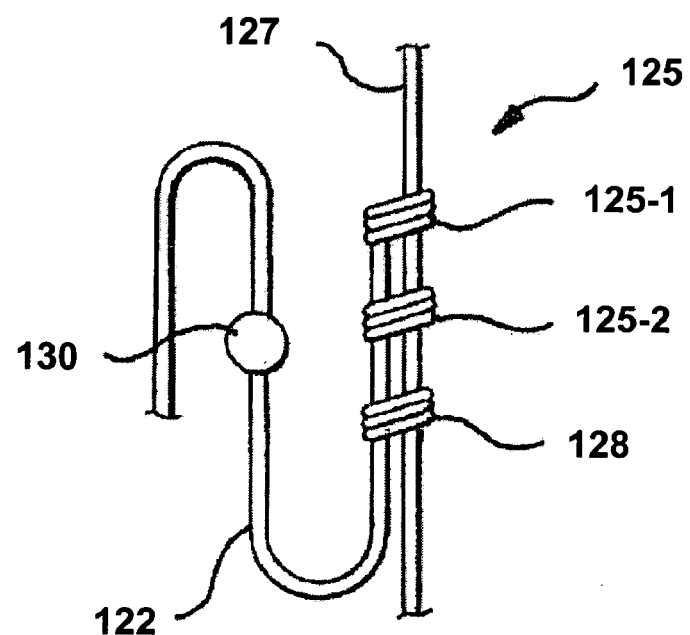

A stimulating nerve electrode assembly 125, preferably comprising an electrode pair, is conductively connected to the distal end of an insulated, electrically conductive lead assembly 122, which preferably comprises a pair of lead wires (one wire for each electrode of an electrode pair). Lead assembly 122 is attached at its proximal end to connectors on the header 116 (FIG. 1C) on case 121. The electrode assembly 125 may be surgically coupled to a vagus nerve 127 in the patient's neck or at another location, e.g., near the patient's diaphragm. Other cranial nerves may also be used to deliver the electrical neurostimulation signal. The electrode assembly 125 preferably comprises a bipolar stimulating electrode pair 125-1, 125-2 (FIG. 1D), such as the electrode pair described in U.S. Pat. No. 4,573,481 issued Mar. 4, 1986 to Bullara. Suitable electrode assemblies are available from Cyberonics, Inc., Houston, Tex., USA as the Model 302 electrode assembly. However, persons of skill in the art will appreciate that many electrode designs could be used in the present invention. The two electrodes are preferably wrapped about the vagus nerve, and the electrode assembly 125 may be secured to the nerve 127 by a spiral anchoring tether 128 (FIG. 1D) such as that disclosed in U.S. Pat. No. 4,979,511 issued Dec. 25, 1990 to Reese S. Terry, Jr. and assigned to the same assignee as the instant application. Lead assembly 122 is secured, while retaining the ability to flex with movement of the chest and neck, by a suture connection 130 to nearby tissue (FIG. 1D).

In one embodiment, the open helical design of the electrode assembly 125 (described in detail in the above-cited Bullara patent), which is self-sizing and flexible, minimizes mechanical trauma to the nerve and allows body fluid interchange with the nerve. The electrode assembly 125 preferably conforms to the shape of the nerve, providing a low stimulation threshold by allowing a large stimulation contact area with the nerve. Structurally, the electrode assembly 125 comprises two electrode ribbons (not shown), of a conductive material such as platinum, iridium, platinum-iridium alloys, and/or oxides of the foregoing. The electrode ribbons are individually bonded to an inside surface of an elastomeric body portion of the two spiral electrodes 125-1 and 125-2 (FIG. 1D), which may comprise two spiral loops of a three-loop helical assembly. The lead assembly 122 may comprise two distinct lead wires or a coaxial cable whose two conductive elements are respectively coupled to one of the conductive electrode ribbons. One suitable method of coupling the lead wires or cable to the electrodes 125-1, 125-2 comprises a spacer assembly such as that disclosed in U.S. Pat. No. 5,531,778, although other known coupling techniques may be used.

The elastomeric body portion of each loop is preferably composed of silicone rubber, and the third loop 128 (which typically has no electrode) acts as the anchoring tether for the electrode assembly 125.

In certain embodiments of the invention, sensors such as eye movement sensing electrodes 133 (FIG. 1B) may be implanted at or near an outer periphery of each eye socket in a suitable location to sense muscle movement or actual eye movement. The electrodes 133 may be electrically connected to leads 134 implanted via a catheter or other suitable means (not shown) and extending along the jaw line through the neck and chest tissue to the header 116 of the electrical pulse generator 110. When included in systems of the present invention, the sensing electrodes 133 may be utilized for detecting rapid eye movement (REM) in a pattern indicative of a disorder to be treated, as described in greater detail below. The detected indication of the disorder can be used to trigger active stimulation.

Other sensor arrangements may alternatively or additionally be employed to trigger active stimulation. Referring again to FIG. 1B, electroencephalograph (EEG) sensing electrodes 136 may optionally be implanted and placed in spaced-apart relation on the skull, and connected to leads 137 implanted and extending along the scalp and temple, and then connected to the electrical pulse generator 110 along the same path and in the same manner as described above for the eye movement electrode leads 134.

In alternative embodiments, temperature sensing elements and/or heart rate sensor elements may be employed to trigger active stimulation. In addition to active stimulation incorporating sensor elements, other embodiments of the present invention utilize passive stimulation to deliver a continuous, periodic or intermittent electrical signal (each of which constitutes a form of continual application of the signal) to the vagus nerve according to a programmed on/off duty cycle without the use of sensors to trigger therapy delivery. Both passive and active stimulation may be combined or delivered by a single IMD according to the present invention. Either or both modes may be appropriate to treat the particular disorder diagnosed in the case of a specific patient under observation.

The electrical pulse generator 110 may be programmed with an external computer 150 using programming software of the type copyrighted by the assignee of the instant application with the Register of Copyrights, Library of Congress, or other suitable software based on the description herein, and a programming wand 155 to facilitate radio frequency (RF) communication between the computer 150 (FIG. 1A) and the pulse generator 110. The wand 155 and software permit non-invasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator.

A variety of stimulation therapies may be provided in implantable medical systems 100 of the present invention. Different types of nerve fibers (e.g., A, B, and C fibers being different fibers targeted for stimulation) respond differently to stimulation from electrical signals. More specifically, the different types of nerve fibers have different conduction velocities and stimulation thresholds and, therefore, differ in their responsiveness to stimulation. Certain pulses of an electrical stimulation signal, for example, may be below the stimulation threshold for a particular fiber and, therefore, may generate no action potential in the fiber. Thus, smaller or narrower pulses may be used to avoid stimulation of certain nerve fibers (such as C fibers) and target other nerve fibers (such as A and/or B fibers, which generally have lower stimulation thresholds and higher conduction velocities than C fibers). Additionally, techniques such as pre-polarization may be employed wherein particular nerve regions may be polarized before a more robust stimulation is delivered, which may better accommodate particular electrode materials. Furthermore, opposing polarity phases separated by a zero current phase may be used to excite particular axons or postpone nerve fatigue during long term stimulation.

As used herein, the terms "stimulating" and "stimulator" may generally refer to delivery of a signal, stimulus, or impulse to neural tissue for affecting neuronal activity of a neural tissue (e.g., a volume of neural tissue in the brain or a nerve). The effect of such stimulation on neuronal activity is termed "modulation"; however, for simplicity, the terms "stimulating" and "modulating", and variants thereof, are sometimes used interchangeably herein. The effect of delivery of the stimulation signal to the neural tissue may be excitatory or inhibitory and may potentiate acute and/or long-term changes in neuronal activity. For example, the effect of "stimulating" or "modulating" a neural tissue may comprise on one more of the following effects: (a) changes in neural tissue to initiate an action potential (bi-directional or unidirectional); (b) inhibition of conduction of action potentials (endogenous or externally stimulated) or blocking the conduction of action potentials (hyperpolarizing or collision blocking), (c) affecting changes in neurotransmitter/neuromodulator release or uptake, and (d) changes in neuro-plasticity or neurogenesis of brain tissue. Applying an electrical signal to an autonomic nerve may comprise generating a response that includes an afferent action potential, an efferent action potential, an afferent hyperpolarization, an efferent hyperpolarization, an afferent sub-threshold depolarization, and/or an efferent sub-threshold depolarization.

Embodiments of the present invention provide for performing an override of one or more safety features based upon one or more external inputs received by the IMD. For example, the IMD may receive various inputs that could prompt a temporary interruption or deviation from normal stimulation operation (i.e., deviation from an operational mode). For example, a magnet may be placed proximate to the IMD, which may be an indication that the patient or a physician desires to alter the normal operation (operational mode) of the IMD. The amount of time that the magnet is detected may determine the type of deviation from the normal operation that will occur. Various devices, such as a Reed Switch or a Hall Effect sensor may be employed to detect a magnetic field in order to react to a magnet being placed proximate to the IMD.

Embodiments of the present invention provide for overriding the presence of a magnetic field using various techniques. For example, software techniques may be used to override the presence of a reaction to the presence of a magnetic field based on an earlier input or another indication provided to the IMD. Other techniques, such as hardware, firmware circuits, etc., may be used to monitor a register to determine whether to ignore the interruption data deciphered by a magnetic sensor. This may be beneficial when the patient enters a magnetic field area, such as an MRI field or other electromagnetic location(s).

Further, an external input received by the IMD may be used to temporarily alter the normal operation of the MD. For example, the patient may desire to temporarily stop any stimulation activity. An input from the patient (e.g., a magnetic input) may be used to suspend stimulation activity. Alternatively, an input from the patient may prompt the IMD to enter into reduced stimulation mode, wherein a background signal that does not cause certain stimulation side-effects, may be implemented. The amount of time to employ the alternative stimulation mode, as well as the type of alternative stimulation mode, may be pre-programmed into the IMD.

Figure 2:
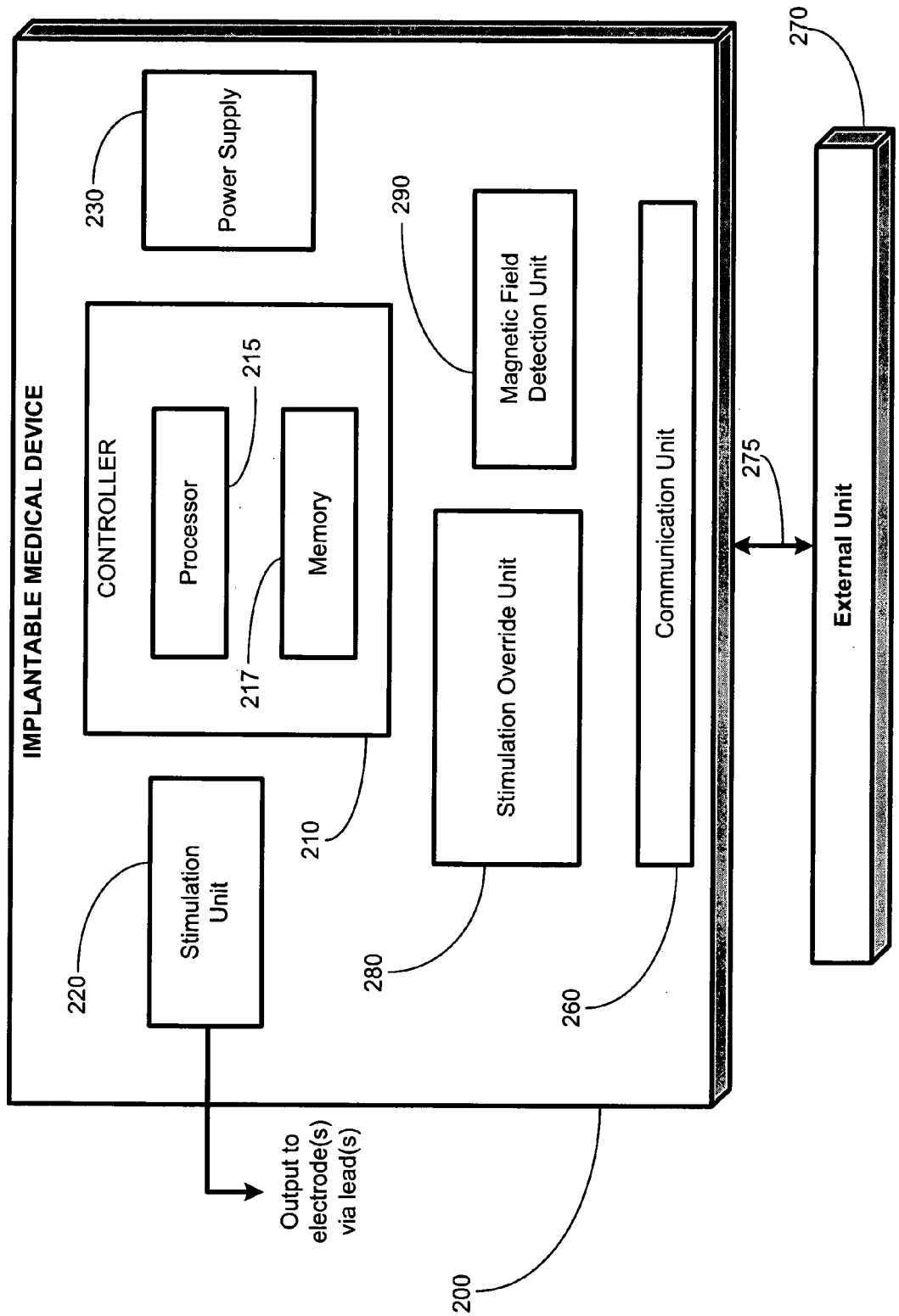
FIG. 2 illustrates a block diagram depiction of the implantable medical device of FIG. 1, in accordance with one illustrative embodiment of the present invention.

Turning now to FIG. 2, a block diagram depiction of an implantable medical device, in accordance with one illustrative embodiment of the present invention is illustrated. The IMD 200 may be used for stimulation to treat various disorders, such as epilepsy, depression, bulimia, heart rhythm disorders, etc. The IMD 200 may be coupled to various leads, e.g., 122, 134, 137 (FIGS. 1A, 1B, 1D). Stimulation signals used for therapy may be transmitted from the IMD 200 to target areas of the patient's body, specifically to various electrodes associated with the leads 122. Stimulation signals from the IMD 200 may be transmitted via the leads 122 to stimulation electrodes associated with the electrode assembly 125 (FIG. 1A). Further, signals from sensor electrodes, e.g., 133, 136 (FIG. 1B) associated with corresponding leads, e.g., 134, 137, may also traverse the leads back to the IMD 200.

The IMD 200 may comprise a controller 210 capable of controlling various aspects of the operation of the IMD 200. The controller 210 is capable of receiving internal data and/or external data and generating and delivering a stimulation signal to target tissues of the patient's body. For example, the controller 210 may receive manual instructions from an operator externally, or may perform stimulation based on internal calculations and programming. The controller 210 is capable of affecting substantially all functions of the IMD 200.

The controller 210 is capable of detecting an input that may prompt the controller 210 to operate in an operational mode (normal mode) or alternatively, in an override mode. When the controller 210 determines that a magnetic input has been received and the IMD 200 is in an override mode, normal delivery of therapeutic neurostimulation signals may be provided. However, when the controller 210 determines that a magnetic input has been received and the IMD 200 is in an operational or normal mode, the controller may cause the delivery of an alternative stimulation signal. The alternative stimulation signal may be a zero current signal, a zero voltage signal, a background signal, or a stimulation signal with an altered frequency, amplitude, pulse width, polarity, phase, off-time, and/or on-time.

The controller 210 may comprise various components, such as a processor 215, a memory 217, etc. The processor 215 may comprise one or more micro controllers, micro processors, etc., that are capable of executing a variety of software components. The memory 217 may comprise various memory portions, where a number of types of data (e.g., internal data, external data instructions, software codes, status data, diagnostic data, etc.) may be stored. The memory 217 may store various tables or other database content that could be used by the IMD 200 to implement the override of normal operations. The memory 217 may comprise random access memory (RAM) dynamic random access memory (DRAM), electrically erasable programmable read-only memory (EEPROM), flash memory, etc.

The IMD 200 may also comprise a stimulation unit 220. The stimulation unit 220 is capable of generating and delivering a variety of electrical neurostimulation signals to one or more electrodes via leads. The stimulation unit 220 is capable of generating a therapy portion, a ramping-up portion, and a ramping-down portion of the stimulation signal. A number of leads 122, 134, 137 may be coupled to the IMD 200. Therapy may be delivered to the leads 122 by the stimulation unit 220 based upon instructions from the controller 210. The stimulation unit 220 may comprise various types of circuitry, such as stimulation signal generators, impedance control circuitry to control the impedance "seen" by the leads, and other circuitry that receives instructions relating to the type of stimulation to be performed. The stimulation unit 220 is capable of delivering a controlled current stimulation signal to the leads and to the electrodes the leads 122.

The IMD 200 may also comprise a power supply 230. The power supply 230 may comprise a battery, voltage regulators, capacitors, etc., to provide power for the operation of the IMD 200, including delivering the stimulation signal. The power supply 230 comprises a power-source battery that in some embodiments may be rechargeable. In other embodiments, a non-rechargeable battery may be used. The power supply 230 provides power for the operation of the IMD 200, including electronic operations and the stimulation function. The power supply 230, may comprise a lithium/thionyl chloride cell or a lithium/carbon monofluoride cell. Other battery types known in the art of implantable medical devices may also be used.

The IMD 200 also comprises a communication unit 260 capable of facilitating communications between the IMD 200 and various devices. In particular, the communication unit 260 is capable of providing transmission and reception of electronic signals to and from an external unit 270. The external unit 270 may be a device that is capable of programming various modules and stimulation parameters of the IMD 200. In one embodiment, the external unit 270 comprises a computer system that is capable of executing a data-acquisition program. The external unit 270 may be controlled by a healthcare provider, such as a physician, at a base station in, for example, a doctor's office. The external unit 270 may be a computer, preferably a handheld computer or PDA, but may alternatively comprise any other device that is capable of electronic communications and programming. The external unit 270 may download various parameters and program software into the IMD 200 for programming the operation of the implantable device. The external unit 270 may also receive and upload various status conditions and other data from the IMD 200. The communication unit 260 may be hardware, software, firmware, and/or any combination thereof. Communications between the external unit 270 and the communication unit 260 may occur via a wireless or other type of communication, illustrated generally by line 275 in FIG. 2.

The IMD 200 is capable of delivering stimulation that can be intermittent, periodic, random, sequential, coded, and/or patterned. The stimulation signals may comprise an electrical stimulation frequency of approximately 0.1 to 2500 Hz. The stimulation signals may comprise a pulse width of in the range of approximately 1-2000 micro-seconds. The stimulation signals may comprise current amplitude in the range of approximately 0.1 mA to 10 mA. Stimulation may be delivered through either the cathode (−) electrode or anode (+) electrode. In one embodiment, the various blocks illustrated in FIG. 2 may comprise software unit, a firmware unit, a hardware unit, and/or any combination thereof.

The IMD 200 may also comprise a magnetic field detection unit 290. The magnetic field detection unit 290 is capable of detecting magnetic and/or electromagnetic fields of a predetermined magnitude. Whether the magnetic field results from a magnet placed proximate to the IMD 200, or whether it results from a substantial magnetic field encompassing an area, the magnetic field detection unit 290 is capable of informing the IMD of the existence of a magnetic field.

The magnetic field detection unit 290 may comprise various sensors, such as a Reed Switch circuitry, a Hall Effect sensor circuitry, and/or the like. The magnetic field detection unit 290 may also comprise various registers and/or data transceiver circuits that are capable of sending signals that are indicative of various magnetic fields, the time period of such fields, etc. In this manner, the magnetic field detection unit 290 is capable of deciphering whether the detected magnetic field relates to an inhibitory input or an excitory input from an external source. The inhibitory input may refer to an inhibition of, or a deviation from, normal stimulation operation. The excitory input may refer to additional stimulation or deviation from normal stimulation.

The IMD 200 may also include a stimulation override unit 280. The stimulation override unit 280 is capable of overriding the reaction by the IMD to the detection of a magnetic signal provided by the magnetic field detection unit 290. The stimulation override unit 280 may comprise various software, hardware, and/or firmware units that are capable of determining an amount of time period in which to override the detection of a magnetic field. The stimulation override unit 280 may also contain safety features, such as returning to normal operation despite an override command after a predetermined period of time. The stimulation override unit 280 is capable of preventing false interruption of normal operation due to false magnetic input signals or unintended magnetic input signals. The stimulation override unit 280 may receive an external indication via the communication unit 270 to engage in an override mode for a predetermined period of time.

Figure 3:
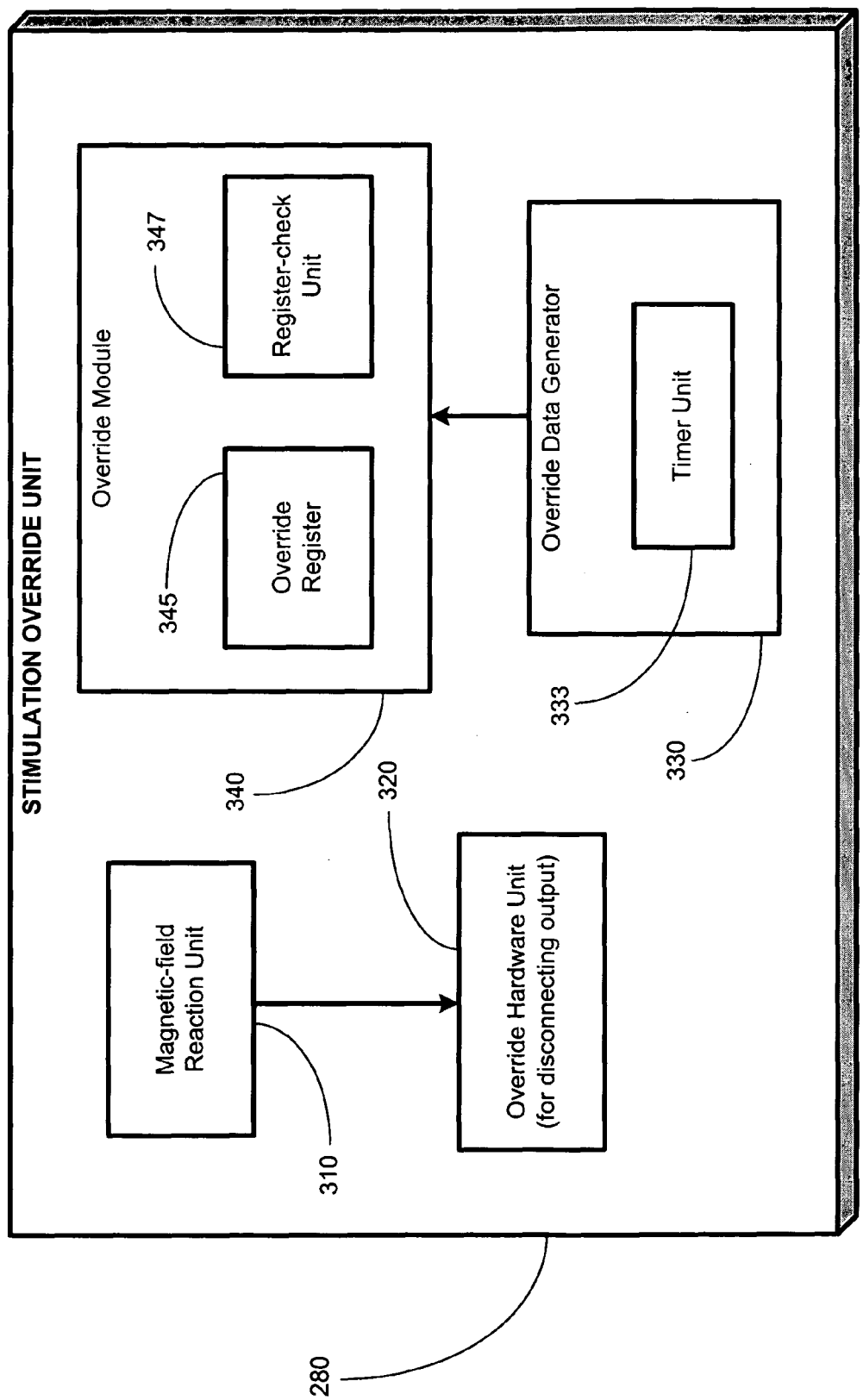
FIG. 3 illustrates a more detailed block diagram depiction of a stimulation override unit of FIG. 2, in accordance with one illustrative embodiment of the present invention.

Turning now to FIG. 3, a more detailed block diagram depiction of the stimulation override unit 280 of FIG. 2, is illustrated. In one embodiment, the stimulation override unit 280 comprises a magnetic field reaction unit 310. The magnetic-field reaction unit 310 may determine how to react to a magnetic field detected by the magnetic-field detection unit 290 (FIG. 2). The magnetic field reaction unit 310 may provide a signal to the IMD 200 to either stop stimulation or to alter the stimulation in some fashion.

The stimulation override unit 280 may also comprise an override hardware unit 320. Based upon data from the magnetic field reaction unit 310, the override hardware unit 320 may disconnect the stimulation signal from the leads or electrodes that may be coupled to the IMD 200. The override hardware unit 320 may comprise various devices, such as switches, registers, multiplexers, etc., that are capable of receiving data and disconnecting stimulation signals to various output ports of the IMD 200, which may be coupled to leads or electrodes.

The stimulation override unit 280 may also comprise an override module 340. The override module 340 is capable of monitoring a predetermined data location to determine whether to continue with an override of a reaction to a magnetic signal. The override module 340 may comprise an override register 345 and a register-check unit 347. The register-check unit 347 is capable of monitoring data in the override register 345. In order to maintain an override mode, data may be written to the override register 345 in a periodic predetermined fashion. The override register 345 is then monitored by the register-check unit 347 at a predetermined frequency. When the override check unit 347 determines that the override register 345 contains the appropriate override data, the override module 340 maintains the override mode of the IMD 200. When the register-check unit 347 determines that the appropriate override data does not exist in the override register 345, the register-check unit 347 may then prompt the override module to exit the override mode and enter into a normal stimulation mode.

The override register 345 may comprise circuitry that, by default, may register "fill" data, e.g., a predetermined string of 0's, 1's, or any combination thereof. (e.g., six consecutive 0's followed by three two 1's). Therefore, an affirmative registering of override data being periodically written into the override register 345 may be required for the override module 340 to maintain the override mode. Therefore, without active, intentional action by the IMD 200 to maintain the override mode, the default may be to fall back to normal stimulation mode.

The stimulation override unit 280 may also comprise an override data generator 330. The override data generator 330 may generate the override data that is registered into the override register 345 in the override module 340. The override data may comprise a predetermined string of data with a specific pattern (e.g., six consecutive 1's followed by two 0's). The override data generator 330 may receive data from the communication unit 260 to prompt the generation of the override mode.

The override data generator 330 may also receive data relating to the time period in which the IMD 200 is to be in an override mode. The override register data generator 330 may comprise a timer unit 333, which is capable of controlling the time period in which the override mode is to be active. Upon indication from the timer unit 333 that the override mode time period has expired, the override data generator 330 stops sending data to the override register 345. Based upon this action, the override register 345 may then be filled with default fill data, such as a stream of 0's. This would prompt the override module 340 to exit the override mode and prompt the IMD 200 to enter a normal operation mode.

Various blocks illustrated in FIG. 3 may be individual modules, such as software modules (e.g., object-oriented code, subroutines, etc.), hardware modules, and/or firmware modules (e.g., programmable gate arrays, ASIC-related modules, hardware description language (HDL) modules, etc.). Alternatively, two or more blocks in FIG. 3 may be merged together into one or more software modules, hardware modules, and/or firmware modules.

Figure 4:
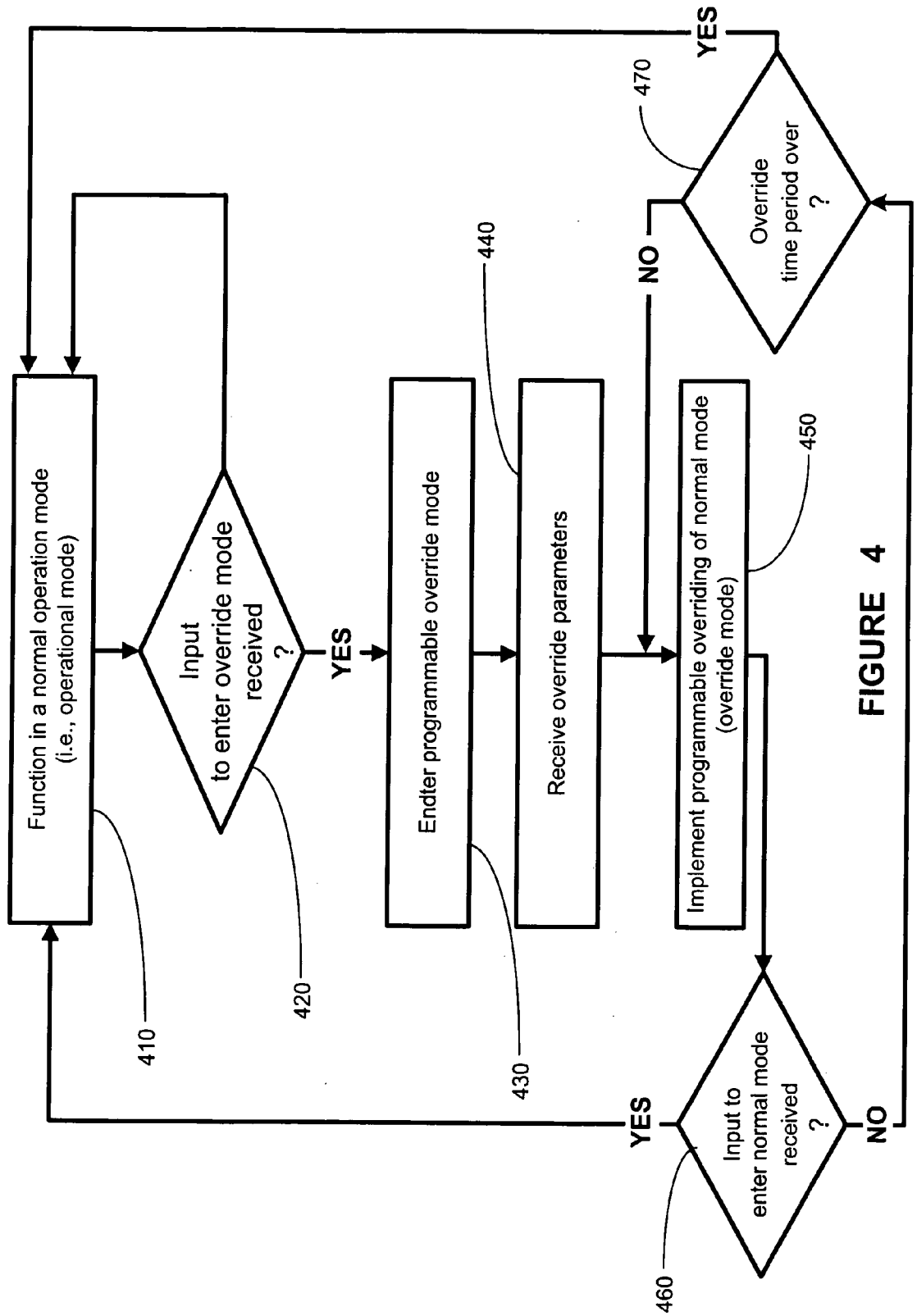
FIG. 4 illustrates a flowchart depiction of a method for performing a stimulation override process, in accordance with a first illustrative embodiment of the present invention.

Turning now to FIG. 4, a flowchart depiction of the method for performing the override mode in accordance with one illustrative embodiment of the present invention is provided. Initially, the IMD 200 may be operating in a normal operation mode, i.e., an operational mode (block 410). The normal operation mode calls for predetermined delivery of stimulation signals followed by inactive or diminished active time periods that are interspersed between actual stimulation cycles. The IMD 200 may then check to determine whether an input to enter an override mode has been received (block 420). If an input to enter an override mode has not been received, normal operation of the IMD and delivery of stimulation signal is resumed (i.e., operational mode is continued), as indicated in FIG. 4. However, if it is determined that an input signal prompting an entry into an override mode has been detected, the IMD 200 may enter a programmable override mode (block 430).

The programmable override mode may refer to a predetermined override mode that may be programmed into the IMD 200 by the patient or a physician. Various inputs to enter the override mode may be provided, such as a magnetic input, a tap input, wireless data transfer via the communication line 375, etc. The IMD 200 may then receive or lookup the relevant override parameters (block 440). Various override parameters may be received, such as the time period for the override, the type of override, e.g., whether a complete shut down of stimulation is required, or whether a modification of the type of stimulation is required.

Upon receiving the override parameters, the IMD 200 implements the programmable override mode. This includes activating the stimulation override unit 280 to cause the IMD 200 to enter into an alternative operation mode (block 450). A determination may then be made whether an input has been received prompting the IMD 200 to go back to a normal mode of operation (block 460). When a determination is made that the normal operation input has not been received, the override programmable mode is continued. Upon a determination that the input to resume normal operation is received, the IMD 200 resumes normal operations. Additionally, upon implementation of the programmable override, a check is made to determine whether the time period for the override mode has expired (block 470). If the time period for the override mode has not expired, the override programmable override mode is continued. However, when the time period for override mode has expired, normal operation is then resumed, as indicated by the path from block 470 to block 410. In this manner, the override function may be programmable and predetermined, wherein a patient entering a magnetic-field area may program the IMD 200 to override magnet response activities for a predetermined period of time.

Figure 5:
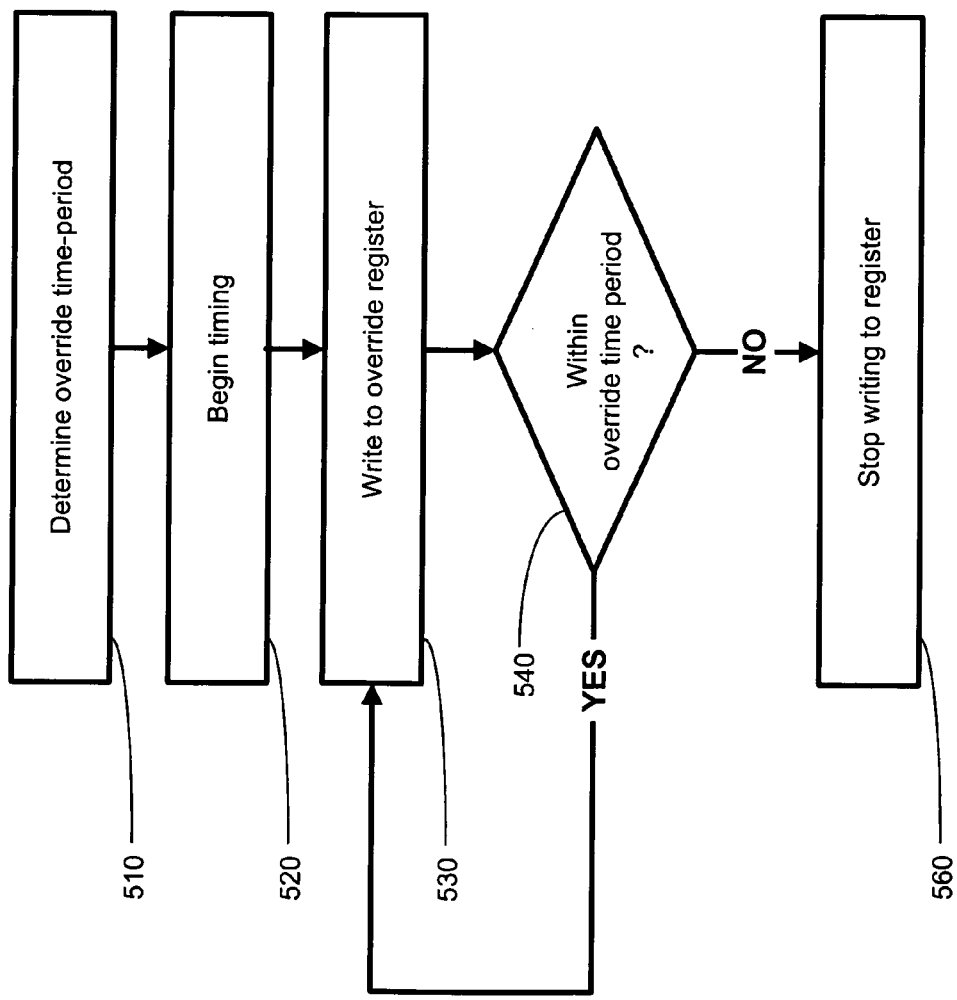
FIG. 5 illustrates a flowchart depiction of the steps for writing to an override register in relation to the stimulation override process of FIG. 4, in accordance with one illustrative embodiment of the present invention.

Turning now to FIG. 5, a flowchart depiction relating to the timing of performing the override mode implementation of FIG. 4, in accordance with one illustrative embodiment of the present invention, is provided. The IMD 200 may determine the override time period (block 510). The override time period may be pre-programmed into the IMD 200 or may be received as an external input. Upon determining the time period for the override mode, the timer unit 333 and the override data generator 330 (FIG. 3) may perform a timing function (block 520).

Upon beginning the timing function, the override data generator 330 may write data into the override register (block 530). The data that is written to the override register may include predetermined override data, which may be indicative of the type of override to perform. This data may be indicative of various types of override that may be performed, such as complete elimination of stimulation, modification of the stimulation cycle pulse width, amplitude, an off-time, an on-time, and the like. Upon writing to the override register 345, a check may be made to determine whether the time period to perform the override mode has expired (block 540). When it is determined that the time period for the override mode has not expired, override data is periodically written into the override register 345 to maintain the override mode. Upon a determination that the time period to perform the override mode has expired, the override register generator 330 stops writing data into the override register (block 560). This would cause default data to be registered into the override register 345, thereby causing the override module 340 to stop the override mode and enter into a normal stimulation mode.

Figure 6:
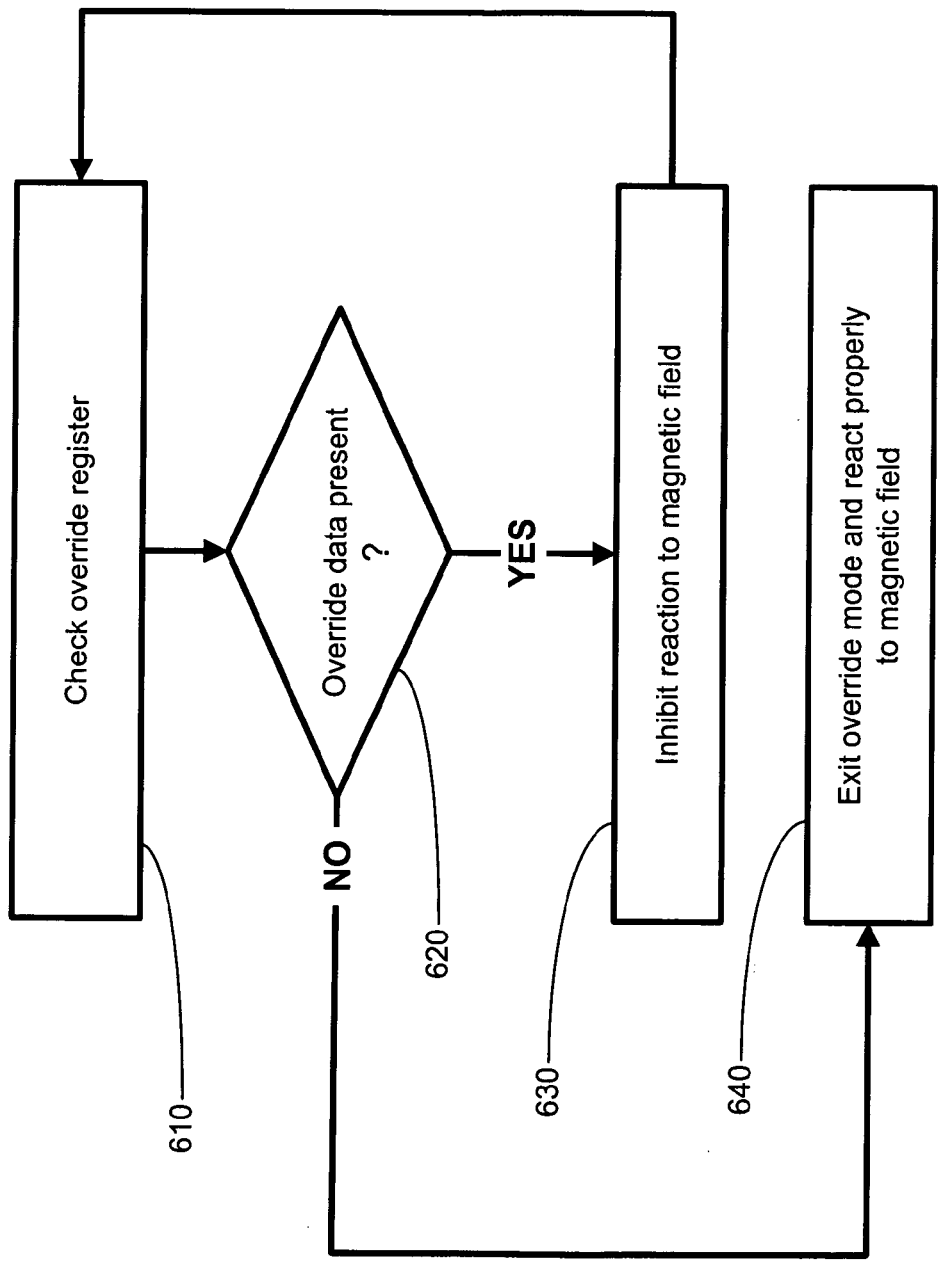
FIG. 6 illustrates a flowchart depiction of the steps for monitoring an override register relating to the stimulation override process of FIG. 4, in accordance with one illustrative embodiment of the present invention.

Turning now to FIG. 6, a flowchart depiction of the step of determining whether to to maintain an override mode, is illustrated. The override module 340 may check the override register 345 to determine what type of data is found (block 610). The override module 340 determines whether override data is present in the override register 345 (block 620). If it is determined that the override data is indeed present in the override register 345, the IMD 200 inhibits the reaction to the magnetic field (block 630). In other words, the IMD 200 continues with normal operation and prevents the normal default safety-stoppage that would have occurred but for the data present in the override register 345.

The override module 340 then continues to check the override register at a predetermined frequency and repeats the process described in block 610, 620 and 630 of FIG. 6. Upon a determination that the override data is not present in the override register, the IMD 200 may exit the override mode and return to normal reaction to the magnetic field (block 640). In other words, the IMD returns to the inhibition or alteration of the normal stimulation process based upon the detection of the magnetic field. In this manner, the patient or a physician may override the predetermined safety features that would have cut-off normal stimulation, or alter normal stimulation based upon the detection of a magnetic signal. Therefore, a patient may enter an area that contains significant amount of electromagnetic signals without undesired interruption of the normal stimulation operations of the IMD 200.

Figure 7:
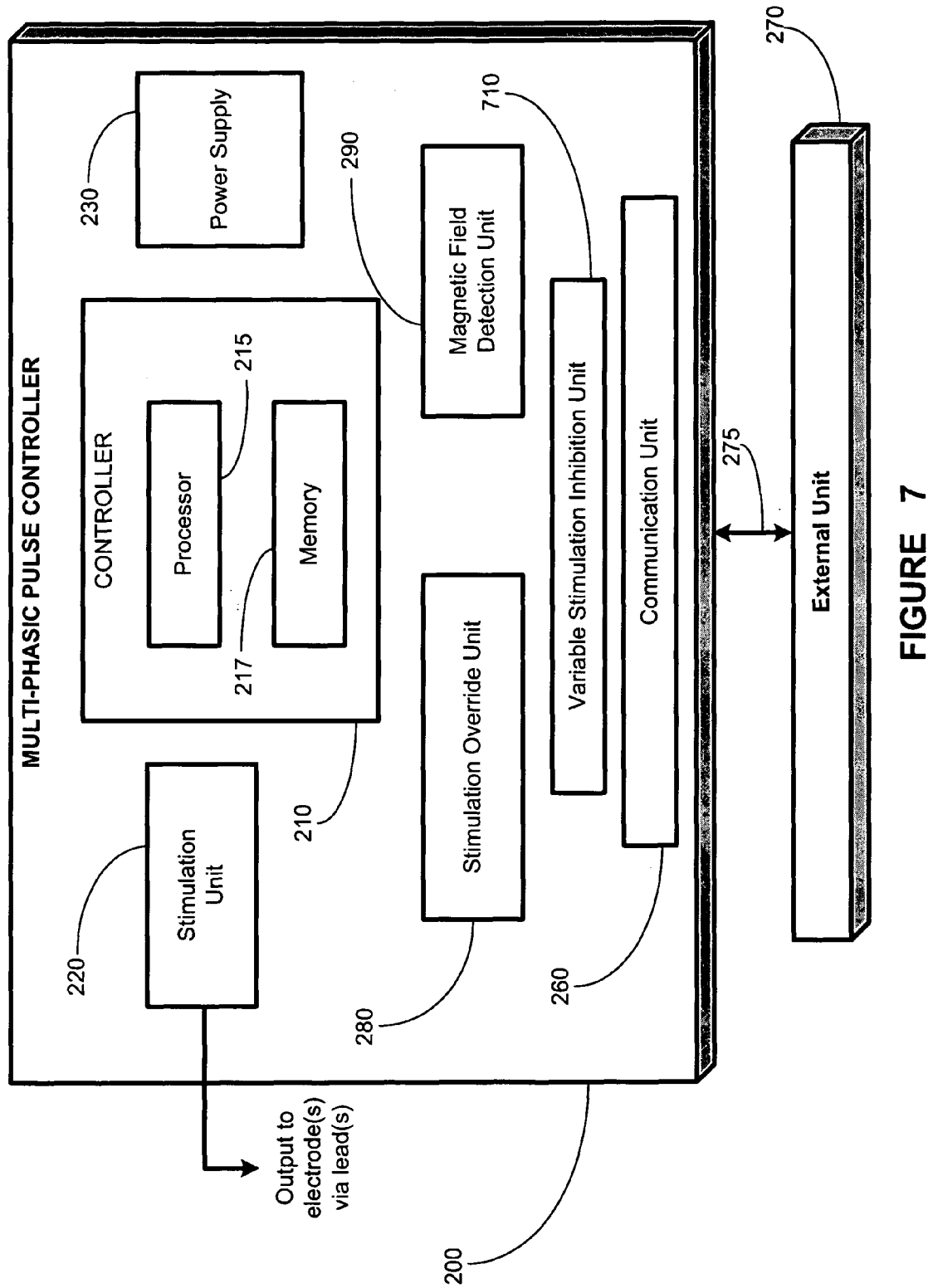
FIG. 7 illustrates a block diagram depiction of the implantable medical device of FIG. 1, in accordance with an alternative illustrative embodiment of the present invention.

Turning now to FIG. 7, a block diagram depiction of the IMD 200, in accordance with an alternative embodiment of the present invention is illustrated. In addition to the various components described in FIG. 2, and the accompanying descriptions above, the illustrative IMD 200 in FIG. 7 also comprises a variable stimulation-inhibition unit 710. The variable stimulation-inhibition unit 710 is capable of performing a variable inhibition of the normal stimulation operation of the IMD 200. Based upon input received by the IMD 200, such as programmed data received through the communication unit 260 from an external source 270 (e.g., the patient, a physician, etc), the IMD 200 is capable of varying the normal stimulation protocol for a controllable, programmable period of time. The variable stimulation-inhibition unit 710 may comprise various software, hardware, and/or firmware units that are capable of monitoring external data to prompt the IMD 200 to enter into alternative stimulation modes. The alternative stimulation modes may include, but is not limited to, a reduced stimulation mode, a background stimulation mode, a stimulation mode with modified parameters (e.g., frequency, phase-characteristics, amplitude, polarity, etc), zero stimulation, etc. A more detailed description of the variable stimulation-inhibition unit 710 is provided below in FIG. 8 and accompanying description below.

Figure 8:
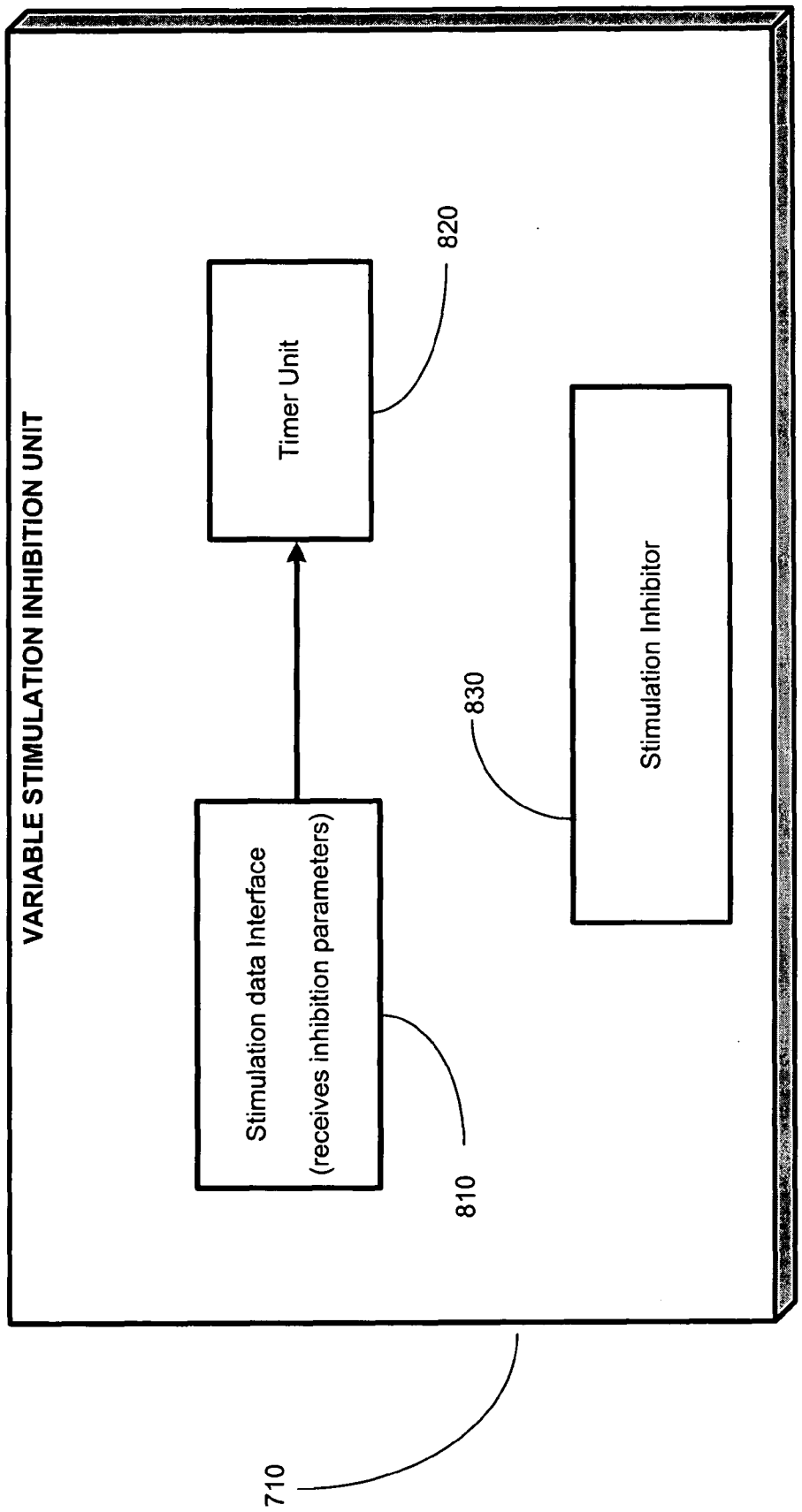
FIG. 8 illustrates a more detailed block diagram depiction of a variable stimulation-inhibition unit of FIG. 7, in accordance with one illustrative embodiment of the present invention.

Turning now to FIG. 8, a more detailed block diagram depiction of the variable stimulation-inhibition unit 710 is illustrated. The variable stimulation-inhibition unit 710 may comprise a stimulation data interface 810. The stimulation data interface 810 is capable of receiving data that may be used to control the type of inhibition or alteration of the normal stimulation process. The stimulation data interface 810 may receive variable stimulation data from an external source. In this manner, the inhibition or alteration of the normal stimulation process may be pre-programmed in a conventional manner or in a real-time fashion. Various parameters, such as the time period of the inhibition or alteration of normal stimulation, the type of alternative stimulation to be delivered (e.g. reduced stimulation or zero stimulation), etc., may be received by the stimulation data interface 810. Based upon the data received by the stimulation data interface 810, a timer circuit 820 in the variable inhibition unit 710 is capable of controlling the time period in which the alternative stimulation period is implemented.

The variable stimulation-inhibition unit 710 also comprises a stimulation inhibitor (block 830). The stimulation inhibitor 830 may comprise various hardware, software, and/or firmware circuitry that are capable of inhibiting or altering the type of stimulation that is delivered to the patient. Based upon the data provided by the stimulation data interface 810, different types of stimulation may be delivered, such as stimulation with an alternative frequency, amplitude, pulse width, polarity, phases, etc., or a complete termination of any stimulation. Additionally, the stimulation inhibitor 830 is capable of implementing a background stimulation mode during the time period determined by the timer unit 820.

The background stimulation may refer to a second electrical signal that is delivered during a second time period, wherein a normal stimulation mode is implemented in a first time period. Embodiments of the present invention may be employed to provide a second electrical signal at a low level, e.g., at a level that is substantially imperceptible to a patient, during a secondary period that may include a portion of the off-time of the first signal. A second electrical signal provided during an off-time of the first signal may be referred to hereinafter as "background" stimulation or modulation. For example, an IMD 200 may apply a second electrical signal having a reduced frequency, current, or pulse width relative to the first electrical signal during off-time of the first period, in addition to the first electrical signal applied during a primary period. Without being bound by theory, applying a background electrical signal may allow the first electrical signal to be reduced to a level sufficient to reduce one or more side effects without reducing therapeutic efficacy.

In some embodiments of the present invention, the first and second time periods at least partially overlap, and a second electrical stimulation signal may be applied during at least a portion of the first time period. In a more particular embodiment, the second time period only partially overlaps the first, and the second electrical stimulation signal is applied during a portion of the first time period and continues during a period in which the first signal is not applied. This type of stimulation is referred to hereinafter as "overlaid" stimulation or modulation. Overlaid and/or background stimulation embodiments of the invention may increase efficacy of a stimulation therapy, reduce side effects, and/or increase tolerability of the first signal to higher levels of stimulation.

Figure 9:
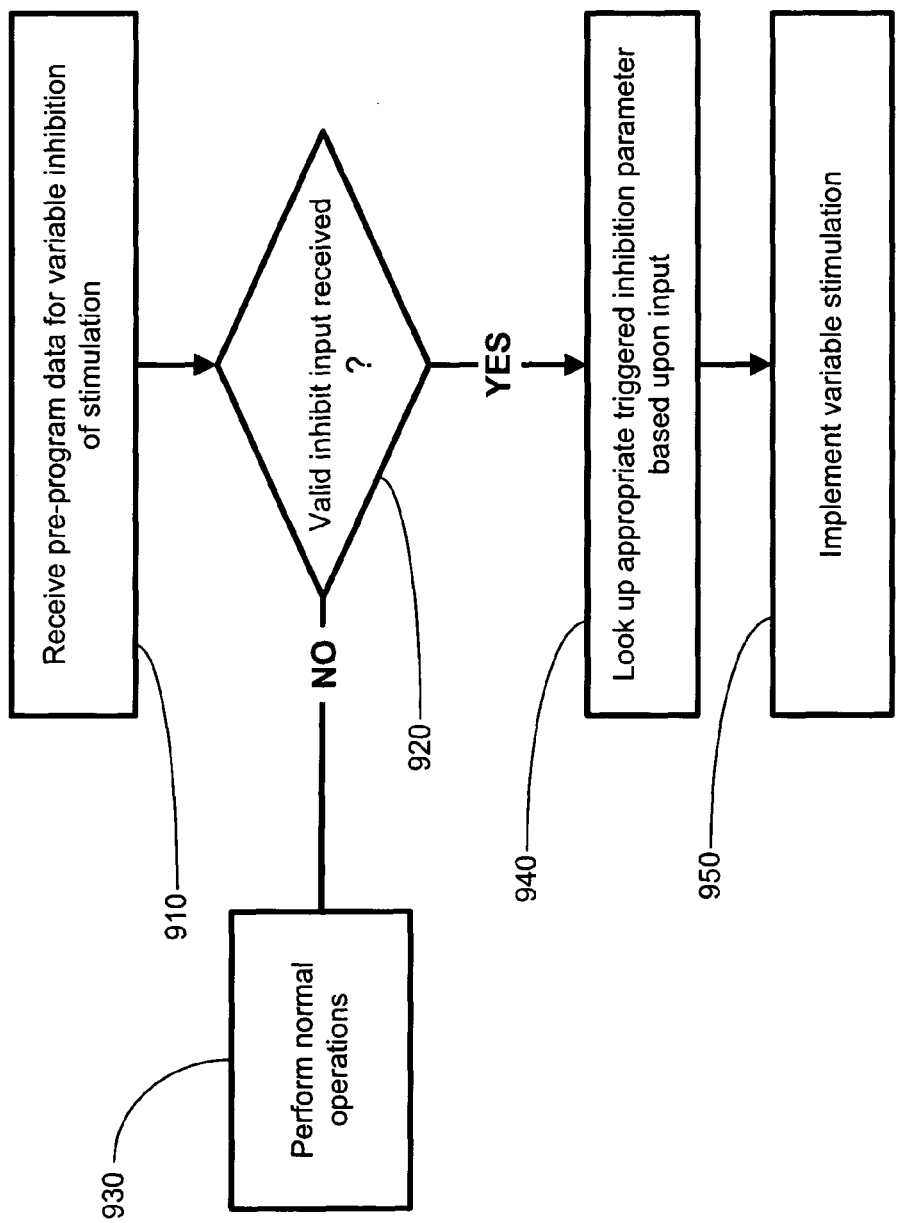
FIG. 9 illustrates a flowchart depiction of a method of implementing a variable stimulation process, in accordance with a second illustrative embodiment of the present invention.

Turning now to FIG. 9, a flowchart depiction of the method of performing the stimulation inhibition mode in accordance with one illustrative embodiment of the present invention, is provided. The IMD 200 may receive pre-programmed data for implementing a variable inhibition of the normal stimulation operation (block 910). This pre-preprogrammed data may include the type of alternative stimulation process to be implemented based upon a predetermined input that may trigger the inhibition mode. For example, a tap or a magnetic input provided by the patient may initiate an inhibition stimulation mode where the normal or current stimulation process is altered. As an example, if a person is scheduled to deliver a speech, due to the concern of interference with the person's voice being altered by the delivery of a stimulation signal, normal stimulation operation may be interrupted for a predetermined duration of time. Alternatively, a background stimulation or a zero stimulation may be performed during the predetermined time period. The predetermined time period and the type of alternative stimulation period to enter may be pre-programmed into the IMD 200.

The IMD 200 determines whether the appropriate inhibition input data is received (block 920). If valid inhibition data input is not received, normal stimulation operation is performed (block 930). However, upon a determination that valid stimulation inhibition input is received, such as a tap input or a predetermined magnetic input for a predetermined duration of time, the IMD 200 may look up the appropriate triggered inhibition parameter based upon the input (block 940). In other words, based upon the type of initiation input received, a particular type of inhibition parameter that may be stored in memory may be retrieved. Based upon the inhibition parameter, a preprogrammed implementation of a variable stimulation inhibition mode may be initiated (block 950). This may include examples such as temporarily shutting off any stimulation, entering a background stimulation mode for a predetermined period of time, etc.

Figure 10:
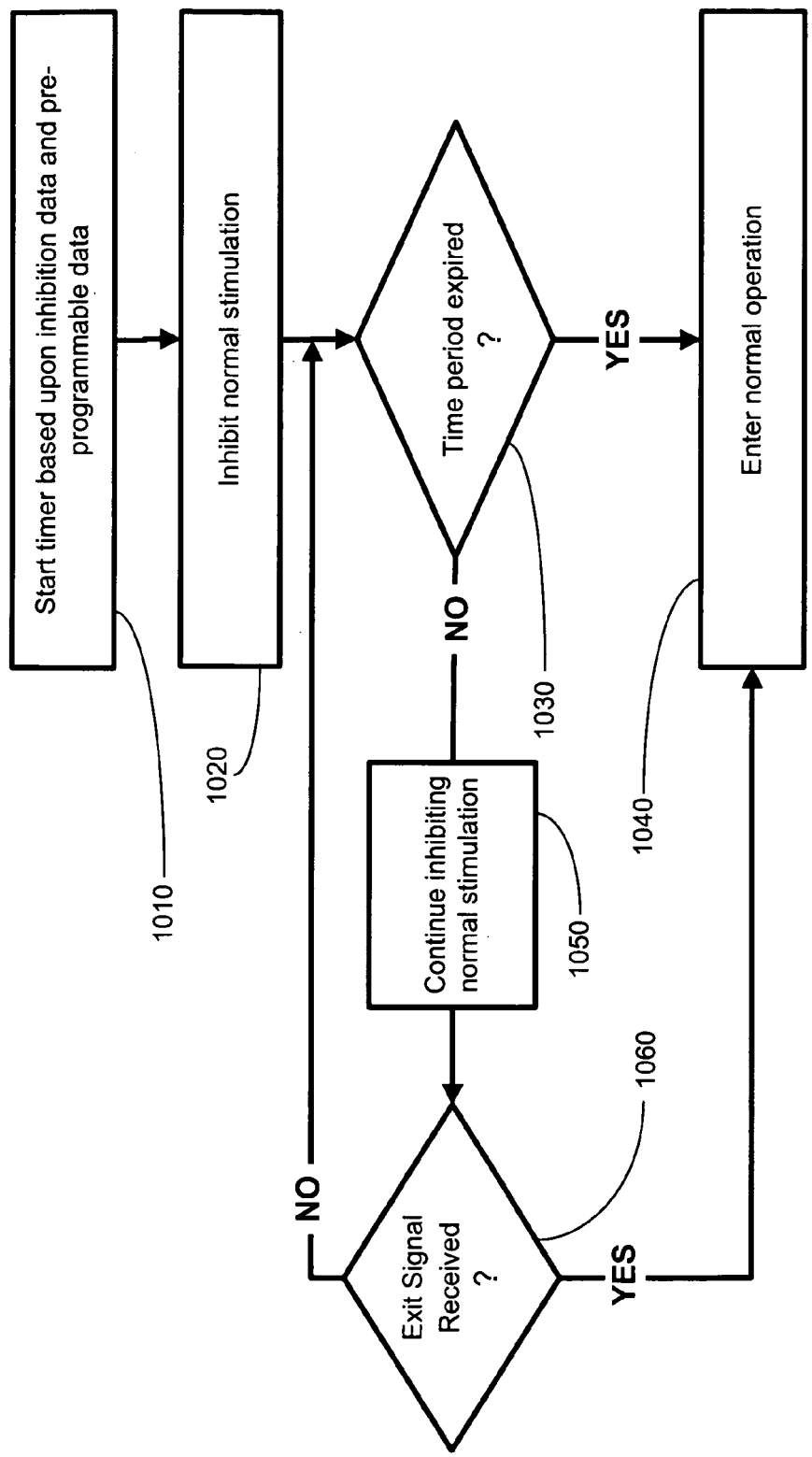
FIG. 10 illustrates a flowchart depiction of the steps for providing the timing for the variable stimulation process of FIG. 9, in accordance with one illustrative embodiment of the present invention.

Turning now to FIG. 10, a flowchart depiction of the timing process relating to the stimulation inhibition process is illustrated. The variable stimulation-inhibition unit 710 may initiate the starting of a timer based upon the inhibition data and the preprogrammed data relating to the inhibition mode (block 1010). For example, based upon the type of input received, and the preprogrammed parameters relating to the particular input, the timer may begin measuring a time period for performing a variable stimulation process. Based upon the time period, the IMD 200 performs inhibition of the normal stimulation process, which may provide for preventing any stimulation or entering into an alternative stimulation mode, such as a background stimulation mode (block 1020).

A determination may then be made as to whether the time period for performing the variable stimulation has expired (block 1030). Based upon an indication that the time period for performing the variable stimulation has expired, the IMD 200 enters into a normal stimulation operation mode (block 1040). Based upon a determination that the time period for the variable stimulation has not expired, the inhibition of the normal stimulation process is continued (block 1050).

A determination may also be made as to whether an external signal to exit the inhibition mode has been received (block 1060). At any time, the patient or the physician may provide a signal to the IMD 200 indicating that the inhibition process is to be terminated and normal stimulation operation is to be resumed. If the signal for exiting the inhibition process has been received, normal stimulation operation is then continued (block 1040). However, if it is determined that the signal for exiting the stimulation process has not been received, the IMD 200 continues to check whether it is within the time period for the inhibition of the normal stimulation process, as illustrated in FIG. 10. In this manner, the alternative stimulation process or the full inhibition of the normal stimulation process is continued until a predetermined time period has expired, or an external input signaling stimulation inhibition has been received. Therefore, a patient can control the inhibition of the normal stimulation process for a predetermined amount of time by analyzing the type of signal that has been sent to the MD 200. Utilizing embodiments of the present invention, flexibility relating to the normal safety reaction to magnetic signal, or inhibition of normal signal stimulation may be achieved by preprogrammed inputs and/or by the input from the patient and/or the physician.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. An implantable medical device (IMD) for providing an electrical neurostimulation therapy to a neural structure of a patient's body and a predetermined response to a magnetic field, comprising:
    a sensor to detect the presence of a magnetic field;
    a controller operatively coupled to said sensor, said controller programmed to implement said predetermined response in response to a detection of said magnetic field; and
    an interface to receive an override signal for placing said IMD into an override mode;
    wherein said controller is operatively coupled to said interface, and said controller is programmed to block said predetermined response to said magnetic field for a preprogrammed period of time in response to receiving said override signal.

2. The implantable medical device of claim 1, comprising:
    a stimulation unit, operatively coupled to said controller, to provide a first stimulation signal and a second stimulation signal;
    a communication unit to provide communication between the IMD and an external device; and
    a stimulation override unit, operatively coupled to said communication unit, to perform an action selected from the group consisting of an alteration of said first stimulation signal to provide said second stimulation signal and maintaining said first stimulation signal.

3. The implantable medical device of claim 2, wherein said stimulation override unit comprises:
    an override data generator to provide override data; and
    an override module comprising:
        an override register to receive at least one of default data and said override data, wherein said default data is generated by default data circuitry, and
        a register check unit to check the content of said override register to determine whether said override register contains at least one of said default data and said override data,
        wherein said override module generates a signal to prompt said IMD to continue an override mode based upon a determination that said override register contains said override data and wherein said override module generates a signal to prompt said IMD to exit an override mode based upon a determination that said override register contains said default data.

4. The implantable medical device of claim 1, wherein said controller further determines whether said magnetic input is detected for a predetermined period of time.

5. The implantable medical device of claim 1, wherein said controller continues a first stimulation signal based upon a determination that said IMD is in an override mode and said controller prompts a second stimulation signal based upon a determination that said IMD is not in an override mode based upon said magnetic input signal.

6. The implantable medical device of claim 3, wherein said default data comprises a predetermined string of digital data.

7. The implantable medical device of claim 3, wherein said override data comprises a predetermined string of digital data.

8. The implantable medical device of claim 1, wherein said magnetic field is a strong magnetic field or a magnetic field generated by a magnetic resonance imaging (MRI) machine.

9. The implantable medical device of claim 2, wherein said magnetic field is a strong magnetic field or a magnetic field generated by a magnetic resonance imaging (MRI) machine.

10. The implantable medical device of claim 4, wherein said magnetic field is a strong magnetic field or a magnetic field generated by a magnetic resonance imaging (MRI) machine.

11. The implantable medical device of claim 1, wherein the override signal is from a magnet mode input, a tap input, or a wireless data transfer.

* * * * *